United States Patent
Belenky et al.

(10) Patent No.: US 11,560,584 B2
(45) Date of Patent: Jan. 24, 2023

(54) PHAGE-MEDIATED IMMUNOASSAY AND METHODS FOR DETERMINING SUSCEPTIBILITY OF BACTERIA TO ANTIBIOTIC OR PROBIOTIC AGENTS

(71) Applicants: QUIDEL CORPORATION, San Diego, CA (US); GUILD ASSOCIATES, INC., Dublin, OH (US)

(72) Inventors: Alexander Solomon Belenky, San Diego, CA (US); David A. Schofield, Hollywood, SC (US)

(73) Assignees: Quidel Corporation, San Diego, CA (US); Guild Associates, Inc., Dublin, OH (US)

( * ) Notice: Subject to any disclaimer, the term of this patent is extended or adjusted under 35 U.S.C. 154(b) by 0 days.

(21) Appl. No.: 15/860,506

(22) Filed: Jan. 2, 2018

(65) Prior Publication Data
US 2018/0187237 A1    Jul. 5, 2018

Related U.S. Application Data

(60) Provisional application No. 62/440,971, filed on Dec. 30, 2016.

(51) Int. Cl.
  *C12Q 1/04*    (2006.01)
  *C12Q 1/18*    (2006.01)
  (Continued)

(52) U.S. Cl.
  CPC ............. *C12Q 1/04* (2013.01); *C12Q 1/18* (2013.01); *C12Q 1/689* (2013.01);
  (Continued)

(58) Field of Classification Search
  None
  See application file for complete search history.

(56) References Cited

U.S. PATENT DOCUMENTS

| | | |
|---|---|---|
| 7,662,594 B2 | 2/2010 | Kong et al. |
| 8,092,990 B2 | 1/2012 | Voorhees |
| 8,501,400 B2 | 8/2013 | Mulvey et al. |
| 8,829,473 B1 | 9/2014 | Griswold et al. |

(Continued)

FOREIGN PATENT DOCUMENTS

| | | |
|---|---|---|
| EP | 0743366 A1 | 11/1996 |
| EP | 1031630 A1 | 8/2000 |

(Continued)

OTHER PUBLICATIONS

Alcaine et al. Phage & phosphatase: a novel phage-based probe for rapid, multi-platform detection of bacteria. Analyst, 2015, 140, 7629-7636 (Year: 2015).*
International Search Report and Written Opinion from International Application No. PCT/US2018/012071, 16 pages, dated Jun. 11, 2018.

(Continued)

*Primary Examiner* — Michelle S Horning
(74) *Attorney, Agent, or Firm* — McDermott Will and Emery LLP; Judy M. Mohr; Brett A. Schweers

(57) ABSTRACT

Methods for determining the susceptibility or resistance of bacteria to antibiotic agents are provided. In one embodiment, the methods include culturing the bacteria in the presence or absence or the antimicrobial agent to generate a primary culture which is then cultured in the presence or absence of transforming phages. The recombinant phages are specific to the bacteria and comprise a heterologous marker (e.g., a nucleic acid that is expressible as a detectable product such as an RNA or a protein). The susceptibility or resistance of the bacteria to the antimicrobial agent may be determined by assaying the culture for the presence or absence of the heterologous marker, wherein a reduction in the level or activity of the marker in the culture compared to (Continued)

the level or activity of the marker in a comparative culture indicates that the bacteria is sensitive to the antibiotic agent.

20 Claims, 2 Drawing Sheets

(51) Int. Cl.
*C12Q 1/689* (2018.01)
*G01N 33/569* (2006.01)
(52) U.S. Cl.
CPC .............. *G01N 33/56911* (2013.01); *G01N 2333/01* (2013.01); *G01N 2333/195* (2013.01); *Y02A 50/30* (2018.01)

(56) References Cited

U.S. PATENT DOCUMENTS

| | | | |
|---|---|---|---|
| 9,133,497 | B2 | 9/2015 | Frei et al. |
| 9,388,453 | B2 | 7/2016 | Rey |
| 9,482,668 | B2 * | 11/2016 | Anderson ........ G01N 33/54326 |
| 2009/0258341 | A1 | 10/2009 | Voorhees et al. |
| 2010/0267044 | A1 | 10/2010 | Franciskovich |
| 2013/0216997 | A1 * | 8/2013 | Anderson ............ G01N 33/581 435/5 |
| 2015/0004595 | A1 * | 1/2015 | Koeris .................... C12Q 1/66 435/5 |
| 2018/0187237 | A1 | 7/2018 | Belenky |
| 2019/0100811 | A1 | 4/2019 | Belenky et al. |

FOREIGN PATENT DOCUMENTS

| | | |
|---|---|---|
| WO | WO 1993/016172 A1 | 8/1993 |
| WO | WO 2005/001475 A2 | 1/2005 |
| WO | WO 2007/035504 A1 | 3/2007 |
| WO | WO 2007/087439 A2 | 8/2007 |
| WO | WO 2012/158502 A2 | 11/2012 |
| WO | WO 2018/126266 A1 | 7/2018 |
| WO | WO 2019/070612 A1 | 4/2019 |

OTHER PUBLICATIONS

Rees and Botsaris "The Use of Phage for Detection, Antibiotic Sensitivity Testing and Enumeration", *Understanding Tuberculosis—Global Experiences and Innovative Approaches to the Diagnosis*, Paragraph: 03.1, Figures,p. 299, InTech, pp. 293-306 (2012).

Van Der Merwe et al., "Phaae-based detection of bacterial pathogens", Analyst. Vol. 139, No. 11, pp. 2617-2626 (2014).

Schmelcher and Loessner, "Application of bacteriophages for detection of foodborne pathogens", Bacteriophage, vol. 4, No. e28137, 14 pages (2014).

Schofield et al., "Phage-based platforms for the clinical detection of human bacterial pathogens", Bacteriophage, vol. 2, No. 2, pp. 105-121 (2012).

Peltomaa et al., "Application of bacteriophages in sensor development", Anal. Bioanal. Chem., vol. 408, No. 7, pp. 1805-1828 (2016).

U.S. Department of Health and Human Services, "Antibiotic Resistance Threats in the United States, 2013", Centers for disease Control and Prevention, No. CS239559-B, pp. 1-18, Acknowledgements pp. 112-113 (2013).

International Search Report from International Application No. PCT/US2018/053812, 6 pages, dated Dec. 7, 2018.

Nithya et al., "Non-protein coding RNA genes as the novel diagnostic markers for the discrimination of *Salmonella* species using PCR", PLoS One, vol. 10, No. 3, pp. 1-16 (2015).

Schofield et al.,"Bacillus anthracis diagnostic detection and rapid antibiotic susceptibility determination using 'bioluminescent' reporter phage", J. Microbiol. Meth., vol. 95, pp. 151-161 (2013).

Tang et al., "Nucleic acid assay system for tier II laboratories and moderately complex clinics to detect HIV in low-resource settings", J. Infect. Dis., vol. 201, Suppl. 1, pp. S46-S51 (2010).

Strambini, "Quenching of alkaline phosphatase phosphorescence by O2 and NO. Evidence for inflexible regions of protein structure", Biophys. J., vol. 52, No. 1, pp. 23-28 (1987).

Talbert et al., "Engineering bacteriophage for a pragmatic low-resource setting bacterial diagnostic platform", Bioengineered, vol. 7, No. 3, pp. 132-136 (2016).

* cited by examiner

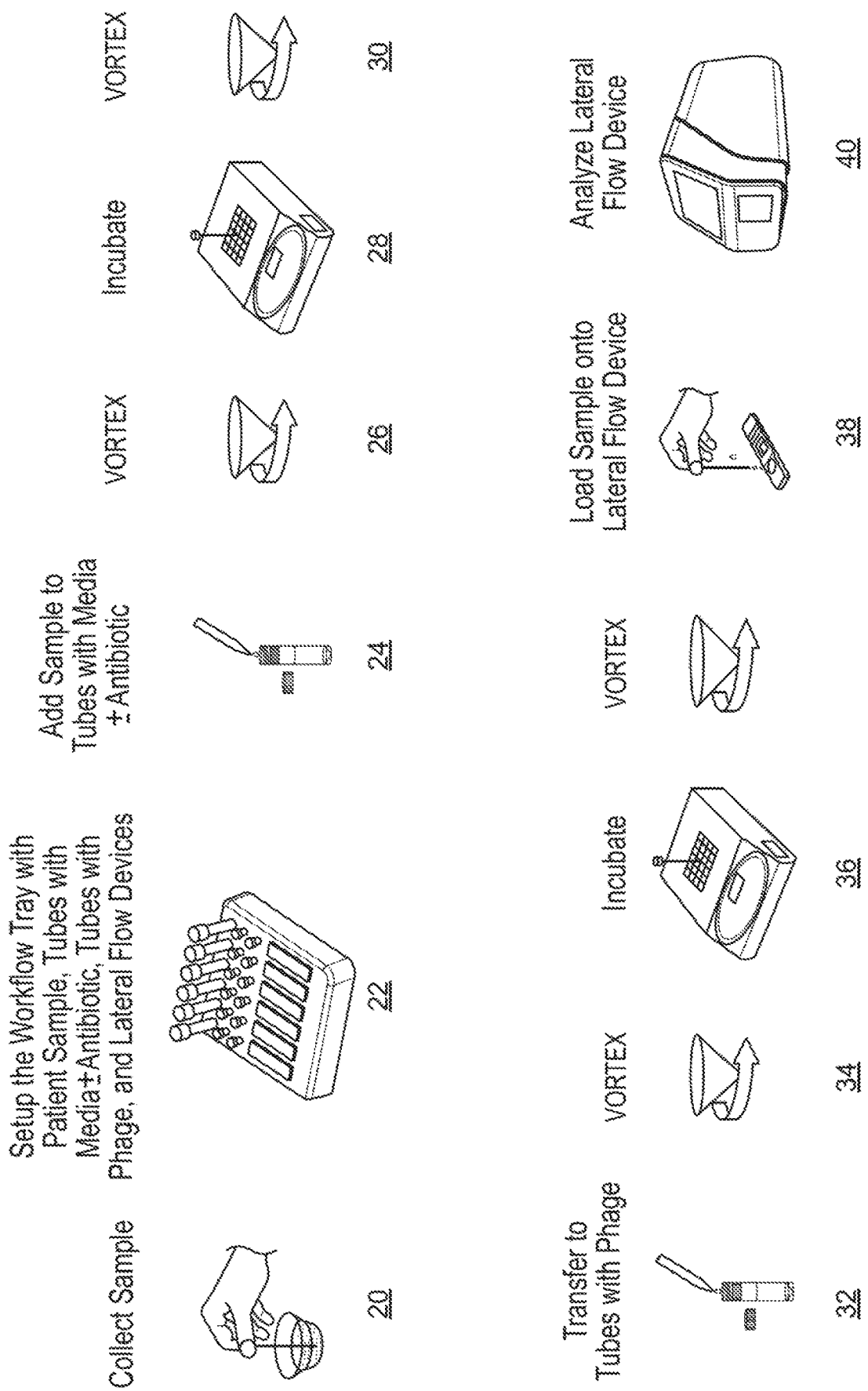

PHAGE-MEDIATED IMMUNOASSAY AND METHODS FOR DETERMINING SUSCEPTIBILITY OF BACTERIA TO ANTIBIOTIC OR PROBIOTIC AGENTS

CROSS-REFERENCE TO RELATED APPLICATIONS

This application claims the benefit of U.S. Provisional Application No. 62/440,971, filed Dec. 30, 2016, incorporated herein by reference in its entirety.

TECHNICAL FIELD

The subject matter described herein relates methods for determining the susceptibility of bacteria to test agents and to methods for the determining whether a target bacterial species is resistant to one or more antimicrobial agents. Further embodiments are directed to methods for screening new test compounds for their antimicrobial or probiotic activity, including, identifying the presence of such agents in biological samples, including food and environmental samples.

BACKGROUND

Since the first practical use of the antibiotic penicillin, many other antibacterial agents have been developed, and antibacterial therapy has greatly contributed to the advancement of modern medicine and the extension of the average lifespan. However, pathogenic bacteria have acquired resistance to a majority of the antibacterial agents, thereby compromising the overall effectiveness of antibacterial therapy while also presenting new public health problems. In particular, methicillin-resistant *Staphylococcus aureus* (MRSA), which demonstrates resistance to β-lactam antibacterial agents, is a highly resistant pathogen. It is directly associated with nearly 94,000 new hospitalizations annually, leading to roughly 19,000 deaths/year in the U.S. alone (Voss et al., *International Journal of Antimicrobial Agents*, 5:101-106, 1995; McGeer et al., *LPTP Newsletter*, 190:1-4, 1996; CDC MRSA tracking). Partly owing to increased use of antibiotics in animal husbandry and hospitals, new strains of multi-drug resistant bacteria are also emerging at an alarming rate. For instance, there have been reports of vancomycin intermediate *S. aureus* (VISA) infections in patients being treated with vancomycin for MRSA infections (Hiramatsu et al., *J Antimicrob Chemother*, 40(1), 135-6, 1997; Périchon et al., *Antimicrob Agents Chemother.*, 53(11):4580-7, 2009). Indeed, some strains have become resistant to practically all of the commonly available agents. A notorious case is the Mu50 strain of MRSA, which is also resistant to aminoglycosides, macrolides, tetracycline, chloramphenicol, and lincosamides (Hiramatsu et al., supra). Multi-drug resistant *Mycobacterium Tuberculosis*, which is resistant to isoniazid and rifampicin, has also been identified (Dalton et al., *Lancet*, 380:1406-17, 2012).

Food-borne bacterial diseases, especially those triggered by drug-resistant bacteria, also pose a significant threat to human health. A microbiological study analyzing 150 food samples comprising vegetable salad, raw egg-surface, raw chicken, unpasteurized milk, and raw meat for *E. coli* revealed that the highest percentages of drug-resistant *E. coli* isolates were detected in raw chicken (23.3%) followed by vegetable salad (20%), raw meat (13.3%), raw egg-surface (10%) and unpasteurized milk (6.7%). The overall incidence of drug resistant *E. coli* was 14.7% (Rasheed et al., *Rev Inst Med Trop Sao* Paulo, 56(4):341-346, 2014). The study further highlights the threat posed by the ability of drug-resistant *E. coli* to transfer drug resistance genes to other species, e.g., *Klebsiella* sp.

Increasing scientific evidence points to how bacteria are evolving defense systems to protect against five major classes of antibacterial drugs that are presently in use. These drugs are broadly categorized as β-lactams, β-lactamase inhibitors, cephalosporins, quinolones, aminoglycosides, tetracyclines/glycylcyclins and polymyxins. The limitations of each agent, especially, when used in singularity, are outlined below.

β-lactams are a large class of broad-spectrum drugs that are the main treatment for gram-negative infections. The subclasses of β-lactam drugs range from narrow-spectrum (penicillin) to broad-spectrum (carbapenem). Gram-negative bacteria have developed several pathways to β-lactam resistance. Perhaps the most concerning mechanism involves evolution of β-lactamases, enzymes that destroy the β-lactam antibiotics. Some β-lactamases destroy narrow spectrum drugs (e.g., only active against penicillin) while newer β-lactamases (e.g., carbapenemases found in carbapenem resistant Enterobacteriaceae or CRE) are capable of neutralizing all β-lactam antibiotics.

β-lactamase inhibitors are still active against gram-negative bacteria that have β-lactamases with limited activity for destroying β-lactam antibiotics. Bacteria that are resistant to extended-spectrum cephalosporins and carbapenems are usually resistant to these drugs as well. New β-lactamase inhibitor combination drugs in development have the potential to overcome some, but not all, of resistance from the most potent β-lactamases such as those found in CRE.

Extended-spectrum cephalosporins have been a cornerstone for treatment of serious gram-negative infections for the past 20 years. Resistant gram-negative infections are spreading into communities. Resistance often leaves carbapenem as the only effective antibacterial agent.

Fluoroquinolones are broad-spectrum antibiotics that are often given orally, making them convenient to use in both inpatients and outpatients. However, with increased use in a patient population drug-resistant strains rapidly evolve, rendering the drug ineffective. Increased use is also associated with an increase in infections caused by resistant, hypervirulent strains of *Clostridium difficile*.

Aminoglycosides are often used in combination with β-lactam drugs for the treatment of infections caused by gram-negative bacteria. Despite growing resistance concerns, these drugs continue to be an important therapeutic option as a last resort against serious infections. However, they are rarely, if ever, used alone by clinicians because of concerns with resistance and their prolonged side effects.

Tetracyclines are not a first-line treatment option for serious gram negative infections; however, with limited efficacy of other drug classes, they are considered an option for treating serious infections. Glycylcyclines (i.e., tigecycline) are often considered for treatment of multidrug-resistant gram-negative infections. Tigecycline is a drug that does not distribute evenly in the body, so it is often used in combination with other drugs depending upon the site of infection. Although relatively uncommon, there have been reported incidences of strains that are resistant to tigecycline.

Polymyxins are an older class that fell out of favor because of toxicity concerns. Now they are often used as a "last resort" agent for treatment of multi-drug resistant gram-negative infections. Because these are generic drugs, there are limited contemporary data on dosimetry and efficacy. Additionally, there is some, but limited data regarding the detection of highly resistant strains.

Given the rapid increase in the number of drug-resistant strains of bacteria, there is an immediate need for new and efficient methods for identifying and karyotyping both clinical and non-clinical isolates of bacteria, particularly, those belonging to the ESKAPE group (*Enterococcus faecium, Staphylococcus aureus, Klebsiella pneumoniae, Acinetobacter baumannii, Pseudomonas aeruginosa* and *Enterobacter* species). (Boucher et al., *Clinical Infectious Diseases*, 48:1-12, 2009). Rapid and accurate pathogen identification is also needed to allow physicians to react and respond appropriately to infections, including those that are potentially life threatening. Currently, pathogen identification requires culture on solid medium (agar-based plate), followed by diagnostic analysis that normally requires additional rounds of replication in culture or purification of a specific bacterial product. At best, microbe identification requires multiple days during which additional levels of biosafety containment may be required depending on the overall classification of the pathogen. Second-generation versions of this biological, growth-based assay speed the time to detection of both microbial identification as well as resistance testing by using radiometric (e.g., Becton Dickinson's BACTEC™) or colorimetric/fluorometric (e.g., Becton Dickinson's MGIT™ and Biomerieux's BACT ALERT®) devices to measure metabolic products produced by growing bacteria, rather than waiting for the bacterial population to reach a density sufficient to be seen by the naked eye. However, these assay systems frequently face contamination problems, thus increasing the need for reprocessing and resulting in unnecessary delays (Tortoli et al., *J. Clin. Microbiol.*, 40:607-610, 2002).

More recent approaches to speed the biological detection of drug resistant bacteria have focused on using bacteriophage to probe the effect an anti-microbial has on an isolate (Schofield et al., *Bacteriophage*, 2(2):105-283, 2012 and WO 08/124119). The phages are used to infect the bacteria, hijack the hosts' cellular biosynthetic machines to replicate, thereby serve as tools for identifying the presence of particular strains of bacteria in clinical specimen. A variety of methods may be employed in the detection of the phage. One method relies on the use of nucleic acid amplification (U.S. Patent Pub. No. 2014-0256664 and WO 12/158502). In this method, drug susceptibility of *M. tuberculosis* is screened by analyzing real-time PCR products of mycobacteriophage D29 DNA.

A related method relies on infecting a secondary culture with the phage-harboring bacteria and analyzing the growth properties of the secondary culture. This method is typically used in identifying drug resistant *M. tuberculosis*. Exemplary commercial kits based on this indirect detection method are sold by Biotec, Inc. (Suffolk, UK) under the mark FASTPLAQUE-RESPONSE™. (Mole et al., *J Med Microbiol.*, 56(Pt 10):1334-9, 2007; Albert et al., *J Appl Microbiol.*, 103(4):892-9, 2007). The kits are also provided with mycobacteriophage D29, however, in contrast to the direct PCR analysis of the D29 DNA, this method attempts to minimize false positives by using a virucide to eliminate phages that did not infect the bacteria. After screening for infected mycobacteria, the phage-infected *M. tuberculosis* is combined with a fast-replicating *M. smegmatis* and the mixture is then plated onto agar dishes. The assay system is based on the principle that *M. smegmatis* is efficiently cross-infected by D29 and forms clear and visible plaques on *M. smegmatis* bacterial lawns, such that each plaque represents an *M. tuberculosis* cell that was initially infected by D29. Thus, the assay quantitatively measures D29 replication in small pool of *M. tuberculosis*. Although an accurate and rapid test, this assay is too complicated and unwieldy for use in resource-poor settings because the analysis of viral growth by plaque formation on agar plates must be performed in a laboratory by a trained technician. Furthermore, the number of secondary fast-growing bacteria that are employable for this assay are limited, the assay cannot be customized or modified to screen for a large number of target bacterial species.

Similarly, variations on the original luciferase reporter assay (LRA), e.g., using engineered mycobacteriophage TM4, are also limited with regard to sensitivity of detection. See, Piuri et al., *PLoS One*, 2009; 4(3):e4870, wherein fluorophages (fluoromycobacteriophages) were able to detect only 50% of *M. tuberculosis* cells 16 h post-infection. Also, because this assay involves detection of fluorescent or luminescent markers expressed in small samples, the assays are limited with respect to types of samples that may be analyzed.

In summary, current approaches to identify drug resistant bacteria fail to satisfy today's need for efficient and effective means for phenotypic analysis of a large variety of bacteria, including, mixtures thereof, for e.g., on the basis of the type of resistance they harbor. There is therefore a pressing need for assay systems that are useful for screening susceptibility of particular strains of bacteria to antibacterial agents. Such assay technology could be effectively combined with the diagnosis, treatment and management of many human and veterinary diseases, such as, cholera, meningitis, pneumonia, etc. Such systems and assays could also be used in the screening of probiotics that can be used to supplement the growth of industrially-useful microbes, e.g., *E. coli, R. eutropha, S. carnosus*, etc.

BRIEF SUMMARY

It is therefore an object to provide less costly, more efficient, more specific, faster, more accessible, and better adaptable processes and apparatuses for selective microbe (e.g., bacterial) detection than provided by currently available technology. Accordingly, a method for determining bacterial resistance to antibiotics and for microbial species identification is provided. The methods exploit the intrinsic specificity of bacteriophages to their corresponding host bacteria. In one embodiment, a method that provides for identification of a bacterial species causing an infection and the simultaneous determination of susceptibility of the identified bacteria to an antimicrobial or antibiotic agent is provided.

In accordance with the foregoing, embodiments provide recombinant bacteriophages, a method for constructing and producing such recombinant bacteriophages, and methods for use of such recombinant bacteriophages for detecting target bacteria and/or determining drugs or antibiotics to which the target bacteria is/are resistant. The compositions and methods may also be adapted to screen for new probiotic agents that are useful for biosynthesis of enzymes, hormones, antibodies, nucleic acids, sugars, and other biomolecules at the laboratory level or on an industrial scale.

In accordance with an embodiment, products, kits, and methods that are capable of detecting specific types of bacteria, for example, by probing for the presence of a specific molecule, e.g., a marker such as protein, in a targeted viable bacterium. Once the drug resistant strains are identified, the methods may, for example, be coupled with other techniques for identifying the molecular basis for drug resistance mechanism, e.g., genetic mutation, gene duplication, transformation, antibiotic degradation, etc. The present utilization of recombinant phages comprising genes of heterologous peptide/protein markers, which are detectable by immunoassay, achieves the aforementioned objectives.

In one embodiment, a method for identifying a bacterial species in a sample is provided. The method comprises culturing or incubating the sample, or an aliquot of the sample, with a bacteriophage transformed to express a heterologous protein marker to form a transformed culture, and assaying the transformed culture for presence or absence of a heterologous protein marker. Presence of the marker indicates presence of the bacteria species. In one embodiment, the assaying is performed using a lateral flow immunoassay.

In one embodiment, the bacteriophage is selected from the group consisting of a lytic bacteriophage, a lysogenic bacteriophage, and a filamentous bacteriophage.

In another embodiment, the lytic bacteriophage is selected from the group consisting of T4, T7, T3, and MS2.

In another embodiment, the lysogenic bacteriophage is a λ phage.

In another embodiment, the filamentous bacteriophage is selected from the group consisting of fl, fd, and M13.

In another embodiment, the marker is expressible into a nucleic acid or a protein in the bacteria.

In another embodiment, the marker is expressible into a polypeptide selected from the group consisting of an antigen, an enzyme, an antibody or a fragment thereof, and an aptamer, or a combination thereof.

In another embodiment, the protein marker comprises a detectable label.

In another embodiment, the protein marker or the detectable label on the marker is detected with an assay selected from a fluorescent assay, a chemiluminescent assay, an enzyme assay, gel electrophoresis, an immunoassay, and a ligand-binding assay.

In another embodiment, the detectable label on the protein marker is detected with a lateral flow immunoassay.

In another embodiment, the incubating further comprises incubating in the presence of an antimicrobial agent, wherein expression of the heterologous protein marker is indicative of bacterial resistance to the antimicrobial agent.

In another aspect, a method for simultaneous identification of a bacteria species in a sample and determination of its susceptibility to an antimicrobial agent is provided. The method comprises (a) culturing a sample or an aliquot of a sample with an antimicrobial agent to generate a primary culture; (b) culturing the primary culture with a transforming phage specific to a bacteria species and which is engineered to express a heterologous marker; and (c) detecting presence or absence of the marker, where presence of the marker indicates presence of the bacteria species in the sample and its resistance to the antimicrobial agent.

In another aspect, a method for simultaneous identification of a bacteria species in a sample and determination of its susceptibility to an antimicrobial agent is provided. The method comprises (a) culturing aliquots of a sample with and without an antimicrobial agent to generate a set of primary cultures; (b) culturing portions of the set of primary cultures with and without a transforming phage specific to a bacteria species and which is engineered to express a heterologous marker, thereby generating a plurality of transformed secondary cultures, wherein a first transformed secondary culture comprises transformed bacteria cultured with antimicrobial agent and a second transformed secondary culture comprises transformed bacteria not cultured with the antimicrobial agent; and (c) detecting presence or absence of the heterologous marker, where presence of the marker indicates presence of the bacteria species in the sample and its resistance to the antimicrobial agent.

In still another aspect, a method for determining a susceptibility of bacteria to a test antimicrobial agent is provided. The method comprises (a) culturing a bacteria in the presence and in the absence of an antimicrobial agent to generate primary cultures; (b) culturing primary cultures in the presence and in the absence of a transforming phage which is specific to the bacteria and which comprises a marker, thereby generating a plurality of transformed secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or an activity of the marker in each of the first and second transformed secondary cultures, thereby determining the susceptibility of the bacteria to the antimicrobial agent.

In one embodiment, a method for determining a susceptibility of bacteria to a test antimicrobial agent is provided, where the method comprises (a) culturing the bacteria in the presence and/or absence of the antimicrobial agent to generate a plurality of primary cultures; (b) culturing the primary cultures of (a) in the presence or absence of a transforming phage which is specific to the bacteria and which comprises a marker, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, thereby determining the susceptibility of the bacteria to the antimicrobial agent. Under this embodiment, steps (a), (b) and (c) can be performed sequentially or non-sequentially. In a particular embodiment, steps (a), (b) and (c) are performed sequentially.

In a related embodiment, a method for the determining a susceptibility of bacteria to a test antimicrobial agent is provided. The method comprises (a) culturing the bacteria in the presence and/or absence of the antimicrobial agent to generate a plurality of primary cultures; (b) culturing the primary cultures of (a) in the presence or absence of a transforming phage which is specific to the bacteria and which comprises a marker, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, wherein a reduction in the level or activity of the marker in the first transformed secondary culture compared to the level or activity of the marker in the second transformed secondary culture (control) indicates that the bacteria is susceptible to the test antimicrobial agent.

In another related embodiment, a method for determining a susceptibility of bacteria to a test antimicrobial agent is provided. The method comprises (a) culturing the bacteria in the presence and/or absence of the antimicrobial agent to generate a plurality of primary cultures; (b) culturing the primary cultures of (a) in the presence or absence of a transforming phage which is specific to the bacteria and which comprises a marker, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, wherein a uniformity (e.g., no change) or an increase in the level or activity of the marker in the first transformed secondary culture compared to the level or activity of the marker in the second transformed secondary culture (control) indicates that the bacteria is not susceptible to or is resistant to the test antimicrobial agent.

In another embodiment, a method for determining a probiotic effect of a test agent on bacteria is provided. The method comprises (a) culturing the bacteria in the presence and/or absence of the agent to generate a plurality of primary cultures; (b) culturing the primary cultures of (a) in the presence or absence of a transforming phage which is specific to the bacteria and which comprises a marker, thereby generating a plurality of secondary cultures, wherein a first transformed secondary culture comprises transformed bacteria that have been treated with the test agent and a second transformed secondary culture comprises transformed bacteria that have not been treated with the test agent; and (c) detecting a level or activity of the marker in each of the first and second transformed secondary cultures, wherein an increase in the level or activity of the marker in the first transformed secondary culture compared to the level or activity of the marker in the second transformed secondary culture (control) indicates that the test agent has a probiotic effect.

In another embodiment, a method for the determining a susceptibility of gram-positive or gram-negative bacteria to a test antimicrobial agent is provided. The method comprises (a) culturing the gram-positive or gram-negative bacteria in the presence and/or absence of the antimicrobial agent to generate a plurality of primary cultures; (b) culturing the primary cultures of (a) in the presence or absence of a transforming phage which is specific to the gram-positive or gram-negative bacteria and which comprises a marker, thereby generating a plurality of secondary cultures, wherein a first transformed secondary culture comprises transformed gram-positive or gram-negative bacteria that have been treated with the test antimicrobial agent and a second transformed secondary culture comprises transformed gram-positive or gram-negative bacteria that have not been treated with the antimicrobial agent; and (c) detecting a level or activity of the marker in each of the first and second transformed secondary cultures, thereby determining the susceptibility of the gram-positive or gram-negative bacteria to the antimicrobial agent.

In one embodiment, the bacteria is selected from the group consisting of *Acinetobacter baumannii, Bacillus anthracis, Bacillus cereus, Bordetella pertussis, Borrelia burgdorferi, Brucella aborus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtherias, Enterobacter* sp., *Enterococcus faecalis*, vancomycin-resistant *Enterococcus faecalis, Enterococcus faecium, Escherichia coli*, enterotoxigenic *Escherichia coli* (ETEC), enteropathogenic *Escherichia coli, E. coli* O157:H7, *Francisella tularensis, Haemophilus influenzae, Helicobacter pylori, Klebsiella pneumoniae, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Proteus, Pseudomonas aeruginosa, Rickettsia rickettsii, Salmonella typhi, Salmonella typhimurium, Shigella sonnei, Staphylococcus aureus, Staphylococcus epidermis, Staphylococcus saprophyticus*, methicillin-resistant *Staphylococcus aureus* (MRSA), vancomycin-resistant *Staphylococcus aureus* (VSA), *Streptococcus agalactiae, Streptococcus pneumoniae, Streptococcus pyogenes, Treponema pallidum, Vibrio cholerae*, and *Yersinia pestis*.

In another embodiment, the bacteria are selected from the group consisting of *Enterococcus* sp., *Escherichia* sp., *Staphylococcus* sp., *Klebsiella* sp., *Acinetobacter* sp., *Pseudomonas* sp. and *Enterobacter* sp.

In another embodiment, a method for determining a susceptibility of bacteria listed in any one of Tables 1-3 to a test antimicrobial agent is provided, the method comprising, (a) culturing the bacteria listed in any one of Tables 1-3 in the presence or absence of the antimicrobial agent to generate a plurality of primary cultures; (b) culturing the primary cultures of (a) in the presence or absence of a transforming phage listed in any one of Tables 1-3, wherein the phage is specific to the bacteria and comprises a sequence for expression of a heterologous marker, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, thereby determining the susceptibility of the bacteria to the antimicrobial agent. Under this embodiment, the bacteria may be selected from the group consisting of *Bacillus anthracis, Bacillus subtilis, Bacillus thuringiensis, Escherichia coli, Lactobacillus delbrueckii, Lactobacillus plantarum, Lactococcus lactis, Listeria monocytogenes, Pseudomonas aeruginosa, Pseudomonas syringae, Klebsiella, Salmonella, Shigella,* and *Staphylococcus aureus*.

In another embodiment, a method for the determining a susceptibility of bacteria to a test antimicrobial agent is provided. The method comprises (a) culturing the bacteria in the presence and/or absence of the antimicrobial agent to generate a plurality of primary cultures; (b) culturing the primary cultures of (a) in the presence or absence of a transforming recombinant or engineered phage which is specific to the bacteria and which comprises a heterologous marker, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, thereby determining the susceptibility of the bacteria to the antimicrobial agent.

In one embodiment, the recombinant or engineered phage may be selected from the group consisting of (a) a lytic or productive phage; (b) a temperate or lysogenic phage; and (c) a filamentous phage.

In one particular embodiment, the recombinant or engineered phage is a lytic or productive phage selected from the group consisting of T4, T7, T3, and MS2. In a second particular embodiment, the recombinant or engineered phage is a temperate or lysogenic phage. In a third particular embodiment, the recombinant or engineered phage is a filamentous phage is selected from the group consisting of f1, fd, and M13. The method may be practiced using a combination of various phages.

In another embodiment, a method for the determining a susceptibility of bacteria to a test antimicrobial agent is provided. The method comprises (a) culturing the bacteria in the presence and/or absence of the antimicrobial agent to generate a plurality of primary cultures; (b) culturing the primary cultures of (a) in the presence or absence of a transforming phage which is specific to the bacteria and which comprises a marker that is expressible into a nucleic acid or a polypeptide product in the bacterial cell, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, thereby determining the susceptibility of the bacteria to the antimicrobial agent. In a particular embodiment, the marker is expressible into a polypeptide selected from the group consisting of an antigen, an enzyme, an antibody or a fragment thereof, and an aptamer, or a combination thereof.

In some embodiments, the expressed polypeptide marker may comprise a detectable label. In other embodiments, the polypeptide marker may be detected with an assay selected from fluorescent assay, chemiluminescent assay, an enzyme assay, gel electrophoresis, an immunoassay, a ligand-binding assay, a chromotrographic assay, spectroscopy, or a combination thereof. Particularly, the expressed polypeptide marker is detected with enzyme-linked immunosorbent assay (ELISA) or a lateral flow immunoassay. In certain embodiments, the methods may further comprise validating the detection results by detecting a secondary marker which is a nucleic acid selected from the group consisting of DNA, RNA or a combination thereof. In such embodiments wherein the initial detection is validated, the secondary nucleic acid marker may be detected with gel-electrophoresis, a nucleic acid amplification technique, such as polymerase chain reaction (PCR), quantitative polymerase chain reaction (qPCR) or a combination thereof.

In another embodiment, a method for the determining a susceptibility of bacteria to a test antimicrobial agent is provided, comprising, (a) culturing the bacteria in the presence or absence of the antimicrobial agent to generate a plurality of primary cultures; (b) culturing the primary cultures of (a) in the presence or absence of a transforming phage which is specific to the bacteria and which comprises a nucleic acid encoding a heterologous protein which is (1) an antigen that binds specifically to an antibody or (2) an enzyme that catalyzes a reaction, thereby generating a plurality of secondary cultures, wherein a first transformed secondary culture comprises transformed bacteria that have been treated with the test antimicrobial agent and a second transformed secondary culture comprises transformed bacteria that have not been treated with the antimicrobial agent; and (c) detecting a level or activity of the marker in each of the first and second transformed secondary cultures, thereby determining the susceptibility of the bacteria to the antimicrobial agent. Under this embodiment, wherein the heterologous protein is (1) an antigen that binds specifically to an antibody, the detection step comprises detecting the level of the protein with an immunoassay. Still under this embodiment, wherein the heterologous protein is (2) an enzyme that catalyzes a reaction, the detection step comprises detecting the activity of the protein with an enzyme assay.

In a related embodiment, a method for screening a test agent for anti-bacterial activity against a target bacterial specimen is provided, comprising, (a) culturing the target bacteria in the presence or absence of the test agent to generate a plurality of primary cultures; (b) culturing the primary cultures of (a) in the presence or absence of a transforming phage which is specific to the bacteria and which comprises a marker, thereby generating a plurality of secondary cultures, wherein a first transformed secondary culture comprises transformed bacteria that have been treated with the test agent and a second transformed secondary culture comprises transformed bacteria that have not been treated with the test agent; and (c) detecting a level or activity of the marker in each of the first and second transformed secondary cultures, wherein a reduction in the level or activity of the marker in the first transformed secondary culture compared to the level or activity of the marker in the second transformed secondary culture (control) indicates that the test agent has anti-bacterial activity.

Another embodiment is a method for determining the presence or absence of an antibiotic agent in a food sample, comprising, (a) culturing the food sample in a plurality of bacterial cultures, wherein the first culture comprises bacteria that are susceptible to the antibiotic and a second culture comprises bacteria that are resistant to the antibiotic, thereby generating a plurality of primary cultures; (b) culturing the primary cultures of (a) in the presence or absence of a transforming phage which is specific to the bacteria and which comprises a marker, thereby generating a plurality of secondary cultures, wherein a first transformed secondary culture comprises transformed bacteria that are susceptible to the antibiotic agent and a second transformed secondary culture comprises transformed bacteria that are resistant to the antibiotic agent; and (c) detecting a level or activity of the marker in each of the first and second transformed secondary cultures, wherein a reduction in the level or activity of the marker in the first transformed secondary culture compared to the level or activity of the marker in the second transformed secondary culture (control) indicates that the food sample comprises the antibiotic agent. Under this embodiment, the susceptible bacteria and the resistant bacteria belong to the same strain. Still further, the resistant bacteria may be a mutant variant of the susceptible bacteria comprising a recombinant gene that confers resistance to the antibacterial agent.

Another embodiment relates to a method for determining a minimal inhibitory concentration (MIC) of an antibacterial agent against a target bacterial specimen, comprising, (a) culturing the target bacteria in the absence of presence different concentrations of the antibacterial agent to generate a plurality of primary cultures; (b) culturing the primary cultures of (a) in the presence or absence of a transforming phage which is specific to the bacteria and which comprises a marker, thereby generating a plurality of secondary cultures, wherein an experimental group comprises transformed bacteria that have been treated with various concentrations of the antibacterial agent and a control group comprises transformed bacteria that have not been treated with the test agent; and (c) detecting a level or activity of the marker in each of the experimental and control groups, wherein the minimal concentration at which the antibacterial agent is capable of reducing the level or activity of the marker compared to a threshold level or activity of the marker in the control group is indicative of the MIC. In a related embodiment, methods for determining an additive, super-additive, synergistic, or antagonistic activity of two or more antibacterial agents are provided, the methods comprising determining the minimal inhibitory concentration (MIC) for each antibacterial agent in accordance with the foregoing and determining the inhibitory effect of a combination comprising minimal inhibitory concentration of each agent in accordance with the foregoing; comparing the inhibitory effect of the combination to that of the singular agents, thereby determining the additive, super-additive, synergistic, or antagonistic activity of two or more antibacterial agents.

Yet another embodiment relates to a method for the diagnosis and treatment of a bacterial disease in a subject in need thereof, comprising, (a) culturing a plurality of subject samples comprising bacteria to generate a plurality of primary bacterial cultures; (b) culturing the primary cultures of (a) in the presence a plurality of transforming phages, each of which is specific to a bacteria and which comprises a nucleic acid encoding a unique polypeptide marker, thereby generating a plurality of secondary cultures; (c) detecting the unique polypeptide marker in the secondary cultures via immunodetection; (d) correlating the detection of the marker with the bacteria; (e) correlating the presence of the bacteria with the bacterial disease; and (f) optionally administering, into the subject, an antibiotic agent that is specific to the detected bacteria, thereby treating the bacterial disease.

BRIEF DESCRIPTION OF THE DRAWINGS

The details of one or more embodiments of the invention are set forth in the accompanying drawings/tables and the description below. Other features, objects, and advantages of the invention will be apparent from the drawings/tables and detailed description, and from the claims.

FIG. 2 shows an exemplary workflow according to another embodiment of a method described herein.

DETAILED DESCRIPTION

Figure 1:
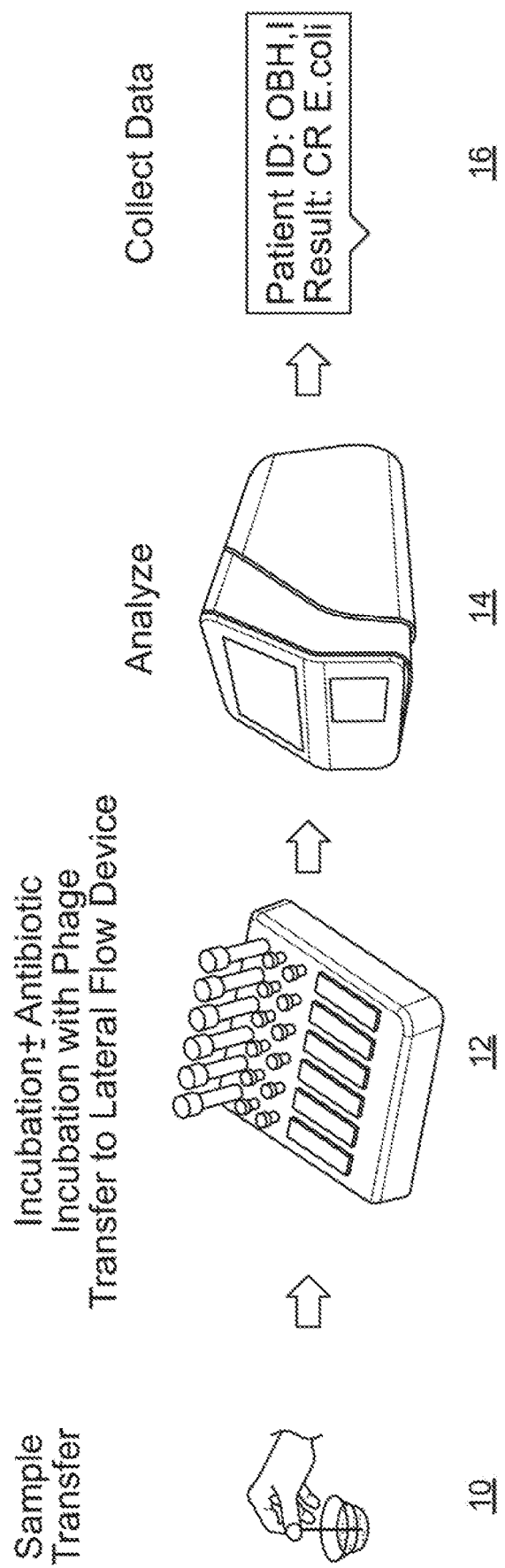
FIG. 1 shows an exemplary workflow according to one embodiment of a method described herein.

Embodiments described herein provide methods and assays for diagnosis or detection of bacterial infectious agents and diseases using recombinant bacteriophages. The methods are suitable for the detection of bacterial infectious agents and also for determining drug resistance of such infectious agents. In addition, the methods are used to provide information concerning the susceptibility of the infectious agents to antimicrobial agents.

A. Infectious Bacteria

Essentially any bacteria can be detected and the methods and compositions can be used for determining antibiotic susceptibility of bacteria or for screening a candidate antibiotic agent that exerts a desirable (e.g., antimicrobial or cytotoxic) effect on target bacteria.

In one embodiment, the bacteria are gram-negative bacteria. Typical gram-negative bacteria include proteobacteria such as *E. coli, Salmonella, Pseudomonas*, and *Helicobacter*, and cyanobacteria. When classified in connection with medicine, they include *Pseudomonas aeruginosa* and *Hemophilus influenzae* causing the disturbance of the respiratory system, *Escherichia coli* and *Proteus mirabilis* causing the disturbance of the urinary system, and *Helicobacter pylori* and *Bacillus Gaertner* causing the disturbance of the alimentary system and micrococci such as *Neisseria meningitidis, Moraxella catarrhalis*, and *Neisseria* gonorrhea.

In another embodiment, the bacteria are gram-positive bacteria. By "gram-positive bacteria" is meant a bacterium or bacteria that contain(s) teichoic acid (e.g., lipoteichoic acid and/or wall teichoic acid), or a functionally equivalent glycopolymer (e.g., a rhamnopolysaccharide, teichuronic acid, arabinogalactan, lipomannan, and lipoarabinomannan) in its cell wall. Non-limiting examples of functionally equivalent glycopolymers are described in Weidenmaier et al., Nature, 6:276-287, 2008. Additional examples of functionally equivalent glycopolymers are known in the art. In some embodiments, a gram positive bacterium is identified using the Gram staining method (e.g., generally including the steps of staining with crystal violet, treating with an iodine solution, decolorizing with alcohol, and counterstaining with safranine, wherein a gram positive bacterium retains the violet stain). Non-limiting examples of gram positive bacteria are described herein. Additional examples of gram-positive bacteria are known in the art. Exemplary methods for detecting or identifying gram-positive bacteria are described herein. Additional methods for detecting or identifying gram-positive bacteria are known in the art The target bacteria include pathogenic bacteria that infect mammalian hosts (e.g., bovine, murine, equine, primate, feline, canine, and human hosts). In one embodiment, the bacteria infect and/or cause diseases in a human host. Examples of such pathogenic bacteria include, e.g., members of a bacterial species such as *Bacteroides, Clostridium, Streptococcus, Staphylococcus, Pseudomonas, Haemophilus, Legionella, Mycobacterium, Escherichia, Salmonella, Shigella, Vibrio*, or *Listeria*. Some clinically relevant examples of pathogenic bacteria that cause disease in a human host include, but are not limited to, *Bacillus anthracis, Bacillus cereus, Bordetella pertussis, Borrelia burgdorferi, Brucella aborus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtherias, Enterococcus faecalis*, vancomycin-resistant *Enterococcus faecalis, Enterococcus faecium, Escherichia coli*, enterotoxigenic *Escherichia coli* (ETEC), enteropathogenic *Escherichia coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Proteus, Pseudomonas aeruginosa, Rickettsia rickettsii, Salmonella typhi, Salmonella typhimurium, Shigella sonnei, Staphylococcus aureus, Staphylococcus epidermis, Staphylococcus saprophyticus*, methicillin-resistant *Staphylococcus aureus* (MRSA), vancomycin-resistant *Staphylococcus aureus* (VSA), *Streptococcus agalactiae, Streptococcus pneumoniae, Streptococcus pyogenes, Treponema pallidum, Vibrio cholerae*, and *Yersinia pestis*.

In another embodiment, the infectious bacteria is selected from the group consisting of *Clostridium difficile*, Carbapenem-Resistant Enterobacteriaceae (CR-*Klebsiella* spp; CR-*E. coli*), and *Neisseria gonorrhoeae*. In another embodiment, the infectious bacteria is selected from the group consisting of multidrug-resistant *Acinetobacter*, drug-resistant *Campylobacter*, extended spectrum β-Lactamase (ESBL)-producing enterobacteriaceae, vancomycin-resistant *enterococcus*, multidrug-resistant *Pseudomonas aeruginosa*, drug-resistant non-typhoidal *Salmonella*, drug-resistant *Salmonella enterica* serovar *Typhi*, drug-resistant *Shigella*, methicillin-resistant *Staphylococcus aureus* (MRSA), drug-resistant *Streptococcus pneumoniae*, and drug-resistant Tuberculosis. In another embodiment, the infectious bacteria is selected from the group consisting of vancomycin-resistant *Staphylococcus aureus*, erythromycin-resistant Group A *Streptococcus*, clindamycin-Resistant Group B *Streptococcus*.

In certain embodiments, the infectious agents are natively found in host subjects. In another embodiment, the infectious agents are invasive species that are foreign to host subjects. Preferably, the hosts are mammals, e.g., a rodent, a human, a livestock animal, a companion animal, or a non-domesticated or wild animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an exemplary embodiment, the subject is a human.

The methods may be used to analyze infectious agents contained in a variety of samples including, e.g., biological sample, research test samples, environmental samples (such as water samples, including water samples selected from natural bodies of water, ponds, community water reservoirs, recreational waters, swimming pools, whirlpools, hot tubs, spas, water parks, naturally occurring fresh waters, and marine surface waters) and industrial samples (such as fermenting inoculums (such as *Lactobacteria*), chemical reagents, culture media, cleaning solutions)

Preferably, the sample is a biological sample comprising bodily fluids, e.g., sputum, tears, saliva, sweat, mucus, serum, semen, urine, stool, vomit, and blood. The sample may include e.g., cerebral spinal fluid (CSF), blood plasma, blood serum, lymph, lung lavage fluid, pleural fluid, etc. In some embodiments, the sample may be obtained from the subject using any known device or method, e.g., swabs, urethral catheters, aspirators, hypodermic needles, thin needle biopsies, hollow needle biopsies, punch biopsies, metabolic cages, and syringes.

In some embodiments, the biological sample is processed for use in the methods described herein. As a non-limiting example, a sputum or airway surface fluid (ASF) is collected in an appropriate vessel, such as a sterile specimen vial. The sample is solubilized using, for example, acetonitrile to a final concentration of about 60%, trifluoroacetic acid to a final concentration of about 0.1%, or using N-acetyl cysteine.

In certain embodiments, the biological sample may be manipulated to culture the bacteria contained therein. The term "culture" means either the cultured cells, the culture supernatant, the mixture thereof, or a culture filtrate if a liquid medium is used; if a solid medium is used, the term "culture" means the mixture of the cells and the medium on which they have grown. For example, if a liquid medium is used, the marker may be recovered from the culture mixture by the following procedures. When the full growth of the bacteria is attained, the culture mixture is subjected to treatment with the antibiotic and/or the phage. Such downstream processes may be intervened by one or more washing and/or separation steps comprising centrifugation or filtration, so as to obtain a crude bacterial preparation that is free from contaminants. The markers may be detected or analyzed at the cellular level (e.g., in situ) or after subjecting the cultures to further processing. For example, wherein the marker is a protein or a DNA in the cytosol, they may be extracted by disrupting cells using a suitable method such as grinding or ultrasonic treatment. Cells may be directly subjected to an ultrasonic treatment in a culture medium so as to disrupt the cells and a crude enzyme solution may be obtained by removing any insoluble matter from the treated solution.

If cultivation is performed on a solid medium, the markers may be analyzed by first manipulating the culture using the following procedure: water is added to the solid medium containing the cultured cells, and any insoluble matter is removed from the mixture either immediately or after disrupting the cells by a suitable means such as ultrasonic treatment. A crude marker preparation may be isolated from the crude lysate by conventional purification techniques, such as organic solvent fractionation, ammonium sulfate fractionation, dialysis, isoelectric precipitation and column chromatography, which may be used either independently or in combination. The level or activity of the marker may be determined using conventional methods, e.g., immunoassays for antigenic protein markers, ligand binding for antibody-like markers, enzymatic assays for enzyme-like markers, nucleic acid hybridization and/or nucleic acid amplification, etc.

Depending on the objective, the cell cultures may be analyzed using routine techniques. For example, the bacteria may be cultured to logarithmic phase (MSSA USA300 and MRSA USA300) and peak logarithmic phage may be detected using conventional techniques, e.g., spectrophotometry. Use of logarithmic phase bacteria may be preferable because they are more likely to be adherent due to higher expression of adhesins and their peptidoglycan layer is likely to be less cross-linked and thick compared to stationary-phase cells and the cells are more metabolically active allowing for faster response to damage. However, optimal conditions may vary from strain to strain. Since different strains are often encountered in a clinical setting, this information is important for assessing the utility of the diagnostic methodology. Although it is contemplated herein that there will be strain variability, it is anticipated that the bacteria will behave similarly enough to permit the use of a single protocol for testing all the strains. This expectation is based on the fact that bacterial families (e.g., staphylococci) are genetically quite similar to each other and thus have similar cell structures, which will be the main component in their responsiveness to the particular phage.

In some embodiments, the methods and compositions are useful for the determination of susceptibility of a microbe, e.g., bacteria. As used herein, the term "susceptibility" refers to the degree to which a bacterial cell is affected by an antibiotic. That is, the cell may not be affected at all, it may have its growth and proliferation slowed or halted without its being killed or it may be killed. Susceptibility also refers to the degree a population of a bacterial species or strain is affected by an antibiotic. In this case, certain highly susceptible cells of the population may be very sensitive and may be killed by very low concentrations of the antibiotic, other less sensitive cells may have their growth and proliferation slowed while others may not be affected at all.

In a related embodiment, the methods and compositions are useful for identifying resistance of a microbe, e.g., bacteria, to an antimicrobial agent or an antibiotic. The term "resistant towards an antibiotic" herein means that a particular bacterial strain, often a mutant strain, is not killed, or killed significantly more slowly compared to the corresponding wild-type strain from which the strain is derived. Resistance can also be reflected by altered growth properties of the mutated and wild-type strains. For example, a low concentration of the antibiotic in the culture medium will prevent or significantly decrease the growth of wild-type strains while the growth of the mutated strains is not affected. The phenotype of a resistant strain, e.g., altered growth, cell division, metabolism, biofilm production, virulence, etc. may be determined using routine techniques, for e.g., growing wild-type and mutant strains under identical conditions to assess a change in the parameter being measured. Sensitive strains may be used as reference standards in the assessment of resistance (positive control).

In one embodiment, the methods are carried out by culturing a bacterial sample in presence of and in the absence of an antibiotic. The culture medium or fermentation medium may be modified or adjusted to meet the demands of the respective strains. Descriptions of culture media for various microorganisms are present in the "Manual of Methods for General Bacteriology" of the American Society for Bacteriology (Washington D.C., USA, 1981). The terms culture medium and fermentation medium or medium are interchangeable.

In its simplest sense, the culture medium contains at least one carbon source (e.g., glucose) and at least one nitrogen source (e.g., nitrate), optionally together with a phosphorus source, e.g., phosphoric acid, potassium phosphate or other phosphate salts. Preferably, the cultured medium is buffered for bacterial growth. The culture medium may additionally comprise salts, e.g., chlorides or sulphates of metals such as, for example, sodium, potassium, magnesium, calcium and iron, such as, for example, magnesium sulphate or iron sulphate, which promote growth and/or metabolic activity. Finally, essential growth factors such as amino acids, for example homoserine and vitamins, for example thiamine, biotin or pantothenic acid, may be added to the culture media, depending on necessity. See, U.S. Pat. No. 9,074,229.

A starter sample containing the bacteria be added to the culture in the form of a single batch or be fed in during the cultivation in a suitable manner, e.g., every 2-4 hours or every 1-3 hours, or every 1, 2, 3, or 4 hours.

The pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8. To control foaming, it is possible to employ antifoams such as, for example, fatty acid polyglycol esters. To maintain the stability of bacteria, it is possible to add to the medium suitable selective substances such as, for example, inducers such as IPTG. The fermentation is preferably carried out under aerobic conditions. In order to maintain these conditions, oxygen or oxygen-containing gas mixtures such as, for example, air are introduced into the culture. In batch or fed-batch processes, the cultivation is preferably continued until an amount of the desired density of the microbes is reached. Detection is carried out spectrophotometrically (absorption, fluorescence). This aim is normally achieved within 2 hours to 160 hours. In continuous processes, longer cultivation times are possible. The activity of the microorganisms results in a concentration (accumulation) of the various markers in the fermentation medium and/or in the cells of the microbes.

Examples of suitable fermentation media can be found inter alia in the U.S. Pat. Nos. 5,770,409; 5,275,940; 5,827,698; 5,756,345; and WO 2007/012078 and WO 2009/043803.

B. Antibiotics

The aforementioned culture media may be supplemented with or without an antibiotic. As used herein, the term "antibiotic" or "antimicrobial agent" refers to a substance that inhibits the growth of or destroys microorganisms. Preferably, the antibiotic is useful in curbing the virulence of an infectious agent and/or treating an infectious disease. Antibiotic also refers to semi-synthetic substances wherein a natural form produced by a microorganism, e.g., yeast or fungus is subsequently structurally modified.

In another embodiment, the culture media may be supplemented with or without a probiotic substance. As used herein, the term "probiotic" refers to a substance that promotes the growth or metabolic activity of microorganisms, e.g., a micronutrient, a growth inducer substance, or a toxin removing substance.

Preferably, the antibiotic is selected from the group consisting of β-lactams (including, β-lactamase inhibitors and cephalosporins), fluoroquinolones, aminoglycosides, tetracyclines and/or glycylcyclines and/or polymyxins. Any combination of antimicrobial agents may also be tested, e.g., at least one β-lactam and at least one fluoroquinolone; at least one aminoglycoside and one cephalosporin; at least one β-lactam and one β-lactamase inhibitor, optionally together with an aminoglycoside, etc.

As used herein, the term "β-lactam" refers to any antibiotic agent which contains a β-lactam ring in its molecular structure. Representative examples include natural and semi-synthetic penicillins and penicillin derivatives, clavulanic acid, carbapenems, cephalosporins, cephamycins and monobactams. These drugs are metabolized by enzymes broadly referred to as "β-lactamases." β-lactamases are organized into four molecular classes (A, B, C and D). Class A enzymes preferentially hydrolyze penicillins; class B enzymes include metalloenzymes that have a broader substrate profile than the others; class C enzymes are responsible for the resistance of gram-negative bacteria to a variety of antibiotics; and class D enzymes are serine hydrolases, which exhibit a unique substrate profile.

Generally, β-lactams are classified and grouped according to their core ring structures, where each group may be divided to different categories. The term "penam" is used to describe the core skeleton of a member of a penicillin antibiotic, e.g., β-lactams containing a thiazolidine rings. Penicillins may include narrow spectrum pinicillins, such as benzathine penicillin, benzylpenicillin (penicillin G), phenoxymethylpenicillin (penicillin V), procaine penicillin and oxacillin. Narrow spectrum penicillinase-resistant penicillins, such as methicillin, dicloxacillin and flucloxacillin. The narrow spectrum beta-lactamase-resistant penicillins may include temocillin. The moderate spectrum penicillins include for example, amoxicillin and ampicillin. The broad spectrum penicillins include the co-amoxiclav (amoxicillin+clavulanic acid). Finally, the penicillin group also includes the extended spectrum penicillins, for example, azlocillin, carbenicillin, ticarcillin, mezlocillin and piperacillin. Synthetic penicillin derivative includes, for example, faropenem.

β-lactams containing pyrrolidine rings are named carbapenams. The carbapenems group includes: biapenem, doripenem, ertapenem, imipenem, meropenem, panipenem and PZ-601.

Cephalosporins and cephamycins include cephalexin, cephalothin, cefazolin, cefaclor, cefuroxime, cefamandole, cefotetan, cefoxitin, cefotaxime, and cefpodoxime. Fourth generation cephalosporins, which are active against Gram positive bacteria, include the cefepime and cefpirome. The cephalosporin class may further include: cefadroxil, cefixime, cefprozil, cephalexin, cephalothin, cefuroxime, cefamandole, cefepime and cefpirome. Cephamycins include, for example, cefoxitin, cefotetan, cefmetazole and flomoxef.

An example of carbacephems is loracarbef. Monobactams, which are active against Gram-negative bacteria include, for example, tigemonam, nocardicin A and tabtoxin. Synthetic cephems include, for example, clavulanic acid and oxacephems such as moxalactam and flomoxef.

Fluoroquinolones act by inhibiting enzymes that are essential for bacterial DNA replication. Representative examples of includes, ciprofloxacin, garenoxacin, gatifloxacin, gemifloxacin, levofloxacin, and moxifloxacin.

Aminoglycosides possess bactericidal activity against most gram-negative aerobic and facultative anaerobic bacilli. Representative examples include, for e.g., kanamycin, amikacin, tobramycin, dibekacin, gentamicin, sisomicin, netilmicin, neomycin B, neomycin C, neomycin E (paromomycin) and streptomycin, including, synthetic derivatives clarithromycin and azithromycin.

Tetracyclines are a subclass of polyketides having an octahydrotetracene-2-carboxamide skeleton. They may be naturally-occurring (e.g., tetracycline, chlortetracycline, oxytetracycline, demeclocycline) or semi-synthetic (e.g., lymecycline, meclocycline, methacycline, minocycline, rolitetracycline). Glycylcyclines (e.g., minocycline/tigecycline) are derived from tetracyclines.

Polymyxins are polypeptide antibiotics that are active against gram-negative bacteria such as *E. coli* and *P. aeruginosa*. Only polymyxin B and polymyxin E (colistin) are used clinically.

In practicing the methods the media may be supplemented with one or more of the aforementioned antibiotics. The concentration of the antibiotic may range vary depending upon the antibiotic and the type of strain tested. Preferably, the dose of the antibiotic is equal to or greater than the minimum inhibitory concentration (MIC) of the particular antibiotic on the particular strain. Methods for determining MICs are known in the art (see, Andrews et al., *J Antimicrob Chemother.*, 48 Suppl 1:5-16, 2001). A representative chart of MICs for 40 or so antimicrobial agents on four bacterial strains (*E. coli, S. aureus, P. aeruginosa*, and *Enterococcus faecalis*) is shown in Table 3 of the Report published by European Committee for Antimicrobial Susceptibility Testing (EUCAST) entitled "Determination of minimum inhibitory concentrations (MICs) of antibacterial agents by broth dilution" (*European Society of Clinical Microbiology and Infections Diseases CMI*, 9, 1-7, 2003).

Generally, the concentration of the antibiotic may be increased for identifying or detecting resistant strains, e.g., by at least 2-fold, at least 5-fold, at least 10-fold, at least 20-fold, at least 50-fold, at least 100-fold, at least 300-fold or even 1000-fold over the baseline MIC. This is particularly effective in instances where the target bacteria and the MIC of the antibiotic on the bacteria are already known. For instance, for *E. coli*, the MIC for most antibiotics may range from about 0.01 mg/L to about 10 mg/L; however, resistant strains may not be susceptible until the concentration is increased, e.g., 10-fold (i.e. 1 log fold)-1000 fold (i.e., 3-log fold) over the base-line levels. In this regard, the final antibiotic concentration may be adjusted accordingly.

Purely for illustrative purposes, the following dosages may be employed—for testing the resistance of bacteria to β-lactams such as amoxicillin, the concentration may range from about 2 mg/L to about 40 mg/L, particularly from about 5 mg/L to about 20 mg/L. See, U.S. Pat. No. 9,347,888. On the other hand, for testing the resistance of bacteria to cloxacillin, the concentration may range between about 25 mg/L and about 300 mg/L. For carbapenem, the concentration may range between 0.05 and 32 mg/L. This includes a range between about 2 mg/L to about 32 mg/L for faropenem and from about 0.05 mg/L to about 2 mg/L for doripenem (see, Woodman et al., *J Med Microbiol.*, 19(1):15-23, 1983). For cephalosporins, the concentration may range between about 1 mg/L to about 20 mg/L, preferably from about 4 mg/L to about 16 mg/L (see, Waterworth, *J Clin Pathol*, 35:1177-1180, 1982).

More particularly, the antibiotics may be used in a concentration of any one of 0.1 mg/mL, 0.5 mg/L, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL 44 mg/mL, 45 mg/mL, 50 mg/mL, 60 mg/mL, 70 mg/mL, 80 mg/m, 90 mg/mL, 100 mg/mL, 150 mg/mL, 200 mg/mL, 250 mg/mL, 300 mg/mL, 400 mg/mL, 500 mg/mL, or more. For example, imipenem and ertapenem may be used in the concentrations of 50, 30, 20, 15, 10, 5 and 1 mg/mL. The dosages may be adjusted similarly for combination of antibiotics, e.g., by first determining MICs (combined agents) for wild-type strains and gradually increase the dosages to identify resistant strain(s).

The bacteria are cultured in presence or absence of the antibiotic for specified time periods, e.g., between 2 hours to 160 hours, particularly between 8 hours to 24 hours, especially between 10 hours to 16 hours. The bacteria may be at their growth phase or stationary phase prior to contact with the bacteriophage. The growth phase is a period characterized by cell doubling, wherein the number of cells in the culture grows exponentially. The stationary phase results from both growth of new bacteria and death of senescent cells, often due to a growth-limiting factor such as the depletion of an essential nutrient or accumulation of waste. Preferably, the bacteria are in growth phase prior to inoculation with the bacteriophage. Methods for determining growth phases of bacteria are known in the art. See, Hall et al., *Mol Biol Evol.*, 31(1):232-8, 2014.

In one embodiment, the bacteria are treated with the antibiotic prior to inoculating with the bacteriophage. The primary culture may be optionally washed, e.g., with a wash buffer, prior to inoculation. Depending on the density of the surviving culture, the primary culture or a wash pellet thereof (obtained after centrifugation of the primary culture) may be re-grown in fresh native media (or antibiotic containing media) that has been inoculated with the bacteriophage.

In another embodiment, the bacteria are inoculated with the bacteriophage simultaneously with treatment with the antibiotic agent. This embodiment may be particularly suited for non-lytic phages.

C. Phages

Embodiments of the instant methods utilize host-specific bacteriophages. As used herein, the term "bacteriophage" has its conventional meaning as understood in the art, e.g., a virus that selectively infects one or more bacteria. Many bacteriophages are specific to a particular genus or species or strain of bacteria. The term "bacteriophage" is synonymous with the term "phage." Bacteriophages may include, but are not limited to, bacteriophages that belong to any of the following virus families: Corticoviridae, Cystoviridae, Inoviridae, Leviviridae, Microviridae, Myoviridae, Podoviridae, Siphoviridae, or Tectiviridae. The bacteriophage may be a lytic bacteriophage or a lysogenic bacteriophage or a filamentous bacteriophage. A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells. A lysogenic bacteriophage is one capable of entering the lysogenic pathway, in which the bacteriophage becomes a dormant, passive part of the cell's genome through prior to completion of its lytic cycle. A filamentous bacteriophage contains a circular single-stranded deoxyribonucleic acid (ssDNA) genome packaged into long filaments. These phages do not reproduce by lysing bacteria; instead, they are secreted into the environment without killing the host.

In one embodiment, the phage is a lytic or productive phage (e.g., T4, T7, T3, and MS2). In another embodiment, the phage is a temperate or lysogenic phage (e.g. λ phage). In yet another embodiment, the phage is a filamentous phage (e.g., f1, fd, and M13). A combination of various phages may also be employed. Phage display techniques are known in the art, e.g., U.S. Pat. Nos. 8,685,893; 7,811,973; and U.S. Patent Publication No. 2002-0044922. Preferably, the phages are capable of transforming the host bacteria. As used herein, the term "transformation" means an introduction of DNA into a host cell such that DNA can be replicated as an extra-chromosomal element or by chromosomal integration. That is, transformation refers to synthetic alteration of genes by introducing a foreign DNA into the cell. As is recognized in the art, the DNA of most bacteria is contained in a single circular molecule, called the bacterial chromosome and one or more plasmids.

The phage is an engineered or a recombinant bacteriophage that serves as a vector for a gene that is foreign to the native phage. As used herein, the term "recombinant phage" or "engineered phage" is one that contains a nucleic acid sequence that is not naturally occurring or has a sequence that is made by an artificial combination of two otherwise separated segments of sequence. This artificial combination may be accomplished by chemical synthesis or artificial manipulation of isolated segments of nucleic acids, for example, by genetic engineering techniques or the use DNA transposition. Similarly, a recombinant protein is one encoded by a recombinant nucleic acid molecule. The term recombinant bacteriophage includes bacteriophages that have been altered solely by insertion of a nucleic acid, such as by inserting a nucleic acid encoding a heterologous protein that serves as a reporter or indicator molecule.

In certain embodiments, the phages are purified phages. The term purified does not require absolute purity; rather, it is intended as a relative term. A purified molecule is one in which the molecule is more enriched than it is in its natural environment, such as a preparation in which the molecule represents at least 50%, at least 60%, at least 80%, at least 90%, at least 99% or greater content of the total content of similar molecules within the sample. For example, a purified sample of recombinant phage is one in which the recombinant phage represents at least 50% of all bacteriophages within the sample.

A listing of pathogenic bacterial genera and their known host-specific bacteriophages is presented in the following paragraphs and preferred types of bacteria-phage pairs are provided in Tables 1-3. Synonyms and spelling variants are indicated in parentheses. Homonyms are repeated as often as they occur (e.g., D, D, d). Unnamed phages are indicated by "NN" beside their genus.

Bacteria of the genus *Actinomyces* are infected by the following phage: Av-1, Av-2, Av-3, BF307, CT1, CT2, CT3, CT4, CT6, CT7, CT8 and 1281.

Bacteria of the genus *Aeromonas* are infected by the following phage: AA-1, Aeh2, N, PM1, TP446, 3, 4, 11, 13, 29, 31, 32, 37, 43, 43-10T, 51, 54, 55R 1, 56, 56RR2, 57, 58, 59.1, 60, 63, Aeh1, F, PM2, 1, 25, 31, 40RR2.8t, (syn=44R), (syn=44RR2.8t), 65, PM3, PM4, PM5 and PM6.

Bacteria of the genus *Bacillus* are infected by the following phage: A, aiz1, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-1, Col1, Cor1, CP-53, CS-1, CS1, D, D, D, D5, ent1, FPB, FP9, PS1, FS2, FS3, FS5, FS8, FS9, G, GH8, GT8, GV-1, GV-2, GT-4, g3, g12, g13, g14, g16, g17, g21, g23, g24, g29, H2, ken1, KK-88, Kum1, Kyu1, J7W-1, LP52, (syn=LP-52), L7, Mex1, MJ-1, mor2, MP-7, MP10, MP12, MP14, MP15, Neo1, No 2, N5, N6P, PBC1, PBLA, PBP1, P2, S-a, SF2, SF6, Sha1, Sil1, SPO2, (syn=ΦSPP1), SPβ, STI, ST1, SU-11, t, Tb1, Tb2, Tb5, Tb10, Tb26, Tb51, Tb53, Tb55, Tb77, Tb97, Tb99, Tb560, Tb595, Td8, Td6, Td15, Tg1, Tg4, Tg6, Tg7, Tg9, Tg10, Tg11, Tg13, Tg15, Tg21, Tin1, Tin7, Tin8, Tin13, Tm3, Toc1, Tog1, tol1, TP-1, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, ρ11, φmed-2, φT, φμ-4, φ3T, φ75, φ105, (syn=φ105), 1A, 1B, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, dar1, den1, DP-7, ent2, FoS1, FoS2, FS4, FS6, FS7, G, gall, gamma, GE1, GF-2, GS1, GT-1, GT-2, GT-3, GT-4, GT-5, GT-6, GT-7, GV-6, g15, 19, 110, IS1, K, MP9, MP13, MP21, MP23, MP24, MP28, MP29, MP30, MP32, MP34, MP36, MP37, MP39, MP40, MP41, MP43, MP44, MP45, MP47, MP50, NLP-1, No. 1, N17, N19, PBS1, PK1, PMB1, PMB12, PMJ1, S, SPO1, SP3, SP5, SP6, SP7, SP8, SP9, SP10, SP-15, SP50, (syn=SP-50), SP82, SST, sub1, SW, Tg8, Tg12, Tg13, Tg14, thu1, thu4, thu5, Tin4, Tin23, TP-13, TP33, TP50, TSP-1, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megaterium*), 4 (*B. sphaericus*), AR13, BPP-10, BS32, BS107, B1, B2, GA-I, GP-10, GV-3, GV-5, g8, MP20, MP27, MP49, Nf, PP5, PP6, SF5, Tg18, TP-1, Versailles, φ15, φ29, 1-97, 837/IV, NN-*Bacillus* (1), Bat10, BSL10, BSL11, BS6, BS11, BS16, BS23, BS101, BS102, g18, mor1, PBL1, SN45, thu2, thu3, Tm1, Tm2, TP-20, TP21, TP52, type F, type G, type IV, NN-*Bacillus* (3), BLE, (syn=θc), BS2, BS4, BS5, BS7, B10, B12, BS20, BS21, F, MJ-4, PBA12, AP50, AP50-04, AP50-11, AP50-23, AP50-26, AP50-27 and Bam35. The following *Bacillus*-specific phage are defective: DLP10716, DLP-11946, DPB5, DPB12, DPB21, DPB22, DPB23, GA-2, M, No. 1M, PBLB, PBSH, PBSV, PBSW, PBSX, PBSY, PBSZ, phi, SPα, type 1 and μ.

Bacteria of the genus *Bacteroides* are infected by the following phage: ad12, Baf-44, Baf-48B, Baf-64, Bf-1, Bf-52, B40-8, F1, β1, φA1, φBr01, φBr02, 11, 67.1, 67.3, 68.1, NN-*Bacteroides* (3), Bf42, Bf71, and BF-41.

Bacteria of the genus *Bordetella* are infected by the following phage: 134 and NN-*Bordetella* (3).

Bacteria of the genus *Borrellia* are infected by the following phage: NN-*Borrelia* (1) and NN-*Borrelia*.

Bacteria of the genus *Brucella* are infected by the following phage: A422, Bk, (syn=Berkeley), BM29, FO1, (syn=FO1), (syn=FQ1), D, FP2, (syn=FP2), (syn=FD2), Fz, (syn=Fz75/13), (syn=Firenze 75/13), (syn=Fi), F1, (syn=F1), F1m, (syn=F1m), (syn=Fim), (syn=F1U), (syn=FiU), F2, (syn=F2), F3, (syn=F3), F4, (syn=F4), F5, (syn=F5), F6, F7, (syn=F7), F25, (syn=F25), (syn=f25), F25U, (syn=F25u), (syn=F25U), (syn=F25V), F44, (syn=F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=F10), (syn=F10), 371/XXIX, (syn=371), (syn=F11), (syn=P11) and 513.

Bacteria of the genus *Burkholderia* are infected by the following phage: CP75.

Bacteria of the genus *Campylobacter* are infected by the following phage: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, Vfi-6, (syn=V19), Vfv-3, V2, V3, V8, V16, (syn=Vfi-1), V19, V20(V45), V45, (syn=V-45) and NN-*Campylobacter* (1).

Bacteria of the genus *Chlamydia* are infected by the following phage: Chp1.

Bacteria of the genus *Clostridium* are infected by the following phage: CAK1, CA5, Ca7, CEβ, (syn=1C), CEγ, Cld1, c-n71, c-203 Tox-, DEβ, (syn=1D), (syn=1Dtox+), HM3, KM1, KT, Ms, NA1, (syn=Na1tox+), PA1350e, Pfo, PL73, PL78, PL81, P1, P50, P5771, P19402, 1Ctox+, 2Ctox-, 2D, (syn=2Dtox+), 3C, (syn=3Ctox+), 4C, (syn=4tox+), 56, III-1, NN-*Clostridium* (61), NB1tox-α1, CA1, HMT, HM2, PF1, P-23, P-46, Q-05, Q-06, Q-16, Q-21, Q-26, Q-40, Q-46, S111, SA02, WA01, WA03, W111, W523, 80, C, CA2, CA3, CPT1, CPT4, c1, c4, c5, HM7, H11/A1, H18/A1, H22/S23, H158/A1, K2/A1, K21/S23, ML, NA2tox-, Pf2, Pf3, Pf4, S9/S3, S41/A1, S44/S23, α2, 41, 112/S23, 214/S23, 233/A1, 234/S23, 235/S23, II-1, II-2, II-3, NN-*Clostridium* (12), CA1, F1, K, S2, 1, 5 and NN-*Clostridium* (8).

Bacteria of the genus *Corynebacterium* are infected by the following phage: CGI1 (defective), A, A2, A3, A110, A128, A133, A137, A139, A155, A182, B, BF, B17, B18, B51, B271, B275, B276, B277, B279, B282, C, cap1, CC1, CG1, CG2, CG33, CL31, Cog, (syn=CG5), D, E, F, H, H-1, hq1, hq2, I1/H33, I1/H33, J, K, K, (syn=Ktox-), L, L, (syn=Ltox+), M, MC-1, MC-2, MC-3, MC-4, MLMa, N, O, ov1, ov2, ov3, P, P, P, RP6, RS29, S, T, U, UB1, ub2, UH1, UH3, uh3, uh5, uh6, (3, (syn=βtox+), βlav64, βvir, γ, (syn=γtox-), γ19, δ, (syn=δtox+), ρ, (syn=ρtox-), φ9, φ984, ω, 1A, 1/1180, 2, 2/1180, 5/1180, 5ad/9717, 7/4465, 8/4465, 8ad/10269, 10/9253, 13/9253, 15/3148, 21/9253, 28, 29, 55, 2747, 2893, 4498 and 5848.

Bacteria of the genus *Enterococcus* are infected by the following phage: DF78, F1, F2, 1, 2, 4, 14, 41, 867, D1, SB24, 2BV, 182, 225, C2, C2F, E3, E62, DS96, H24, M35, P3, P9, SB101, S2, 2BII, 5, 182a, 705, 873, 881, 940, 1051, 1057, 21096C, NN-*Enterococcus* (1), PE1, P1, F3, F4, VD13, 1, 200, 235 and 341.

Bacteria of the genus *Erysipelothrix* are infected by the following phage: NN-*Erysipelothrix* (1).

Bacteria of the genus *Escherichia* are infected by the following phage: BW73, B278, D6, D108, E, E1, E24, E41, FI-2, FI-4, FI-5, HI8A, HI8B, i, MM, Mu, (syn=mu), (syn=Mu1), (syn=Mu-1), (syn=MU-1), (syn=MuI), (syn=mu), O25, PhI-5, Pk, PSP3, P1, P1D, P2, P4 (defective), S1, Wφ, φK13, φR73 (defective), φ1, φ2, φ7, φ92, ψ (defective), 7A, 8φ, 9φ, 15 (defective), 18, 28-1, 186, 299, NN-*Escherichia* (2), AB48, CM, C4, C16, DD-VI, (syn=Dd-Vi), (syn=DDVI), (syn=DDVi), E4, E7, E28, F11, F13, H, H1, H3, H8, K3, M, N, ND-2, ND-3, ND4, ND-5, ND6, ND-7, Ox-1, (syn=OX1), (syn=11F), Ox-2, (syn=Ox2), (syn=OX2), Ox-3, Ox-4, Ox-S, (syn=OX5), Ox-6, (syn=66F), (syn=φ66t), (syn=φ66t-), O111, PhI-1, RB42, RB43, RB49, RB69, S, Sal-1, Sal-2, Sal-3, Sal-4, Sal-5, Sal-6, TC23, TC45, TuII*-6, (syn=TuII*), TuII*-24, TuII*46, TuII*-60, T2, (syn=gamma), (syn=γ), (syn=PC), (syn=P.C.), (syn=T-2), (syn=T2), (syn=P4), T4, (syn=T-4), (syn=T4), T6, T35, α1, 1, 1A, 3, (syn=Ac3), 3A, 3T+, (syn=3), (syn=M1), (syn=φ5), 9266Q, CFO103, HK620, J, K, K1F, m59, no. A, no. E, no. 3, no. 9, N4, sd, (syn=Sd), (syn=SD), (syn=Sd), (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φ1, φ1.2, φ20, φ95, φ263, φ1092, φI, φII, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK620, HK97, (syn=ΦHK97, HK139, HK253, HK256, K7, ND-1, no. D, PA-2, q, S2, T1, (syn=α), (syn=P28), (syn=T-1), (syn=T1), T3C, T5, (syn=T-5), (syn=T5), UC-1, w, β4, γ2, λ, (syn=lambda), (syn=Φλ), ΦD326, φγ, Φ06, Φ7, Φ10, φ80, χ, (syn=χ1), (syn=φχ), (syn=φχ1), 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-f and 933H.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HP1 (*Haemophilus* phage HP1), S2 and N3.

Bacteria of the genus *Helicobacter* are infected by the following phage: HP1 (*Helicobacter pylori* phage HP1) and NN-*Helicobacter* (1).

Bacteria of the genus *Klebsiella* are infected by the following phage: AIO-2, K14B, K16B, K19, (syn=K19), K114, K115, K121, K128, K129, K132, K133, K135, K1106B, K1171B, K1181B, K1832B, AIO-1, AO-1, AO-2, AO-3, FC3-10, K, K11, (syn=K11), K12, (syn=K12), K13, (syn=K13), (syn=K170/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-1, K14B, K18, K111, K112, K113, K116, K117, K118, K120, K122, K123, K124, K126, K130, K134, K1106B, K1165B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=K1181), (syn=K1181B), K1765/1, (syn=K1765/1), K1842B, (syn=K1832B), K1937B, (syn=K1937B), L1, φ28, 7, 231, 483, 490, 632 and 864/100.

Bacteria of the genus *Leptospira* are infected by the following phage: LE1, LE3, LE4 and NN-*Leptospira* (1).

Bacteria of the genus *Listeria* are infected by the following phage: A511, O1761, 4211, 4286, (syn=BO54), A005, A006, A020, A500, A502, A511, A118, A620, A640, B012, B021, B024, B025, B035, B051, B053, B054, B055, B056, B101, B110, B545, B604, B653, C707, D441, HS047, H1OG, H8/73, H19, H21, H43, H46, H107, H108, H10, H163/84, H1312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* are infected by the following phage: 47.

Bacteria of the genus *Mycobacterium* are infected by the following phage: 13, AG1, AL1, ATCC 11759, A2, B.C3, BG2, BK1, BK5, *butyricum*, B-1, B5, B7, B30, B35, Clark, C1, C2, DNAIII, DSP1, D4, D29, GS4E, (syn=GS4E), GS7, (syn=GS-7), (syn=GS7), IPα, lacticola, Legendre, Leo, L5, (syn=:ΦL-5), MC-1, MC-3, MC-4, minetti, MTPH11, Mx4, MyF3P/59a, *phlei*, (syn=*phlei* 1), *phlei* 4, Polonus II, rabinovitschi, *smegmatis*, TM4, TM9, TM10, TM120, Y7, Y10, φ630, 1B, 1F, 1H, 1/1, 67, 106, 1430, B1, (syn=Bo1), B24, D, D29, F-K, F-S, HP, Polonus I, Roy, R1, (syn=R1-Myb), (syn=R1), 11, 31, 40, 50, 103a, 103b, 128, 3111-D, 3215-D and NN-*Mycobacterium* (1).

Bacteria of the genus *Neisseria* are infected by the following phage: Group I, group II and NP1.

Bacteria of the genus *Nocardia* are infected by the following phage: P8, NJ-L, NS-8, N5 and NN-*Nocardia* (1).

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, Pm1, Pm3, Pm4, Pm6, Pm7, Pm9, Pm10, Pm11, Pv2, π1, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/9211b, 9248, 7/R49, 74761322, 7478/325, 7479, 7480, 9000/9402 and 9213/9211a.

Bacteria of the genus *Pseudomonas* are infected by the following phage: Pf1, (syn=Pf-1), Pf2, Pf3, PP7, PRR1, 7s, NN-*Pseudomonas* (1), AI-1, M-2, B17, B89, CB3, Col 2, Col 11, Col 18, Col 21, C154, C163, C167, C2121, E79, F8, ga, gb, H22, K1, M4, N2, Nu, PB-1, (syn=PB1), pfl6, PMN17, PP1, PP8, Psa1, PsP1, PsP2, PsP3, PsP4, PsP5, PS3, PS17, PTB80, PX4, PX7, PYO1, PYO2, PYO5, PYO6, PYO9, PYO10, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, S2, UNL-1, wy, Ya1, Ya4, Ya11, φBE, φCTX, φC17, φKZ, (syn=ΦKZ), φ-LT, (Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, NN-*Pseudomonas* (23), A856, B26, CI-1, CI-2, C5, D, gh-1, F116, HF, H90, K5, K6, K104, K109, K166, K267, N4, N5, O6N-25P, PE69, Pf, PPN25, PPN35, PPN89, PPN91, PP2, PP3, PP4, PP6, PP7, PP8, PP56, PP87, PP114, PP206, PP207, PP306, PP651, Psp231a, Pssy401, Pssy9220, psl, PTB2, PTB20, PTB42, PX1, PX3, PX10, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-1, C22, D3, D37, D40, D62, D3112, F7, F10, g, gd, ge, gf, Hw12, Jb19, KF1, L°, OXN-32P, 06N-52P, PCH-1, PC13-1, PC35-1, PH2, PH51, PH93, PH132, PMW, PM13, PM57, PM61, PM62, PM63, PM69, PM105, PM113, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-10, Pz, SD1, SL1, SL3, SL5, SM, φC5, φC11, φC11-1, φC13, φC15, φMO, φ04, φ11, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, NN-*Pseudomonas* (6), G10, M6, M6a, L1, PB2, Pssy15, Pssy4210, Pssy4220, PYO12, PYO34, PYO49, PYO50, PYO51, PYO52, PYO53, PYO57, PYO59, PYO200, PX2, PX5, SL4, φ03, φ06 and 1214.

Bacteria of the genus *Rickettsia* are infected by the following phage: NN-*Rickettsia* (1).

Bacteria of the genus *Salmonella* are infected by the following phage: b, Beccles, CT, d, Dundee, f, Fels 2, GI, GIII, GVI, GVIII, k, K, i, j, L, O1, (syn=O-1), (syn=O1), (syn=O4), (syn=7), O2, O3, P3, P9a, P10, Sab3, Sab5, San15, San17, SI, Taunton, Vil, (syn=Vil), 9, NN-*Salmonella* (1), N-1, N-5, N-10, N-17, N-22, 11, 12, 16-19, 20.2, 36, 449C/C178, 966A/C259, a, B.A.O.R., e, G4, GIII, L, LP7, M, MG40, N-18, PSA68, P4, P9c, P22, (syn=P22), (syn=PLT22), (syn=PLT22), P22a1, P22-4, P22-7, P22-11, SNT-1, SNT-2, SP6, ViIII, ViIV, ViV, ViVI, ViVII, Worksop, ε15, ε34, 1, 37, 1(40), (syn=φ1[40]), 1, 422, 2, 2.5, 3b, 4, 5, 6, 14(18), 8, 14(6,7), 10, 27, 28B, 30, 31, 32, 33, 34, 36, 37, 39, 1412, SNT-3,7-11, 40.3, c, C236, C557, C625, C966N, g, GV, G5, G173, h, IRA, Jersey, M78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, ViII, φ1, 1, 2, 3a, 3aI, 1010, NN-*Salmonella* (1), N-4, SasL6 and 27.

Bacteria of the genus *Serratia* are infected by the following phage: A2P, PS20, SMB3, SMP, SMP5, SM2, V40, V56, x, DCP-3, (DCP-6, 3M, 10/1a, 20A, 34CC, 34H, 38T, 345G, 345P, 501B, SMB2, SMP2, BC, BT, CW2, CW3, CW4, CW5, L1232, L2232, L34, L.228, SLP, SMPA, V.43, σ, φCW1, ΦCP6-1, ΦCP6-2, ΦCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/10a, L.359 and SMB1.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PE5, P90, SfII, Sh, SHIII, SHIV, (syn=HIV), SHVI, (syn=HVI), SHVIII, (syn=HVIII), SKγ66, (syn=gamma 66), (syn=γ66), (syn=γ66b), SKIII, (syn=SIIIb), (syn=III), SKIV, (syn=SIVa), (syn=IV), SKIVa, (syn=SIVAn), (syn=IVA), SKVI, (syn=KVI), (syn=SVI), (syn=VI), SKVIII, (syn=SVIII), (syn=VIII), SKVIIIA, (syn=SVIIIA), (syn=VIIIA), STVI, STIX, STXI, STXII, S66, W2, (syn=D2c), (syn=D20), φI, φIV1, 3-SO-R, 8368-SO-R, F7, (syn=FS7), (syn=K29), F10, (syn=F S10), (syn=K31), I1, (syn=alfa), (syn=FSα), (syn=K18), (syn=α), 12, (syn=a), (syn=K19), SG35, (syn=G35), (syn=SO-35/G), SG55, (syn=SO-55/G), SG3201, (syn=SO-3201/G), SHII, (syn=HII), SHV, (syn=SHV), SHX, SHX, SKII, (syn=K2), (syn=KII), (syn=SII), (syn=SsII), (syn=II), SKIV, (syn=SIVb), (syn=SsIV), (syn=IV), SKIVa, (syn=SIVab), (syn=SsIVa), (syn=IVa), SKV, (syn=K4), (syn=KV), (syn=SV), (syn=SsV), (syn=V), SKX, (syn=K9), (syn=KX), (syn=SX), (syn=SsX), (syn=X), STV, (syn=T35), (syn=35-

50-R), STVIII, (syn=T8345), (syn=8345-SO-S-R), W1, (syn=D8), (syn=FSD8), W2a, (syn=D2A), (syn=FS2a), DD-2, Sf6, FS1, (syn=F1), SF6, (syn=F6), SG42, (syn=SO-42/G), SG3203, (syn=SO-3203/G), SKF12, (syn=SsF12), (syn=F12), (syn=F12), STII, (syn=1881-SO-R), γ66, (syn=gamma 66a), (syn=Ssγ66), φ2, B11, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), F11, P2-SO-S, SG36, (syn=SO-36/G), (syn=G36), SG3204, (syn=SO-3204/G), SG3244, (syn=SO-3244/G), SHI, (syn=HI), SHVII, (syn=HVII), SHIX, (syn=HIX), SHXI, SHXII, (syn=HXII), SKI, KI, (syn=SI), (syn=SsI), SKVII, (syn=KVII), (syn=SVII), (syn=SsVII), SKIX, (syn=KIX), (syn=SIX), (syn=SsIX), SKXII, (syn=KXII), (syn=SVII), (syn=SsXII), STI, SIII, STIII, STIV, STVII, S70, S206, U2-SO-S, 3210-SO-S, 3859-SO-S, 4020-SO-S, φ3, φ5, φ7, φ8, φ9, φ10, φ11, φ13, φ14, φ18, SHIII, (syn=HIII), SHXI, (syn=HXI) and SXI, (syn=KXI), (syn=SXI), (syn=SsXI), (syn=XI).

Bacteria of the genus *Staphylococcus* are infected by the following phage: A, EW, K, Ph5, Ph9, Ph10, Ph13, P1, P2, P3, P4, P8, P9, P10, RG, SB-1, (syn=Sb-1), S3K, Twort, φSK311, φ812, 06, 40, 58, 119, 130, 131, 200, 1623, STC1, (syn=stc1), STC2, (syn=stc2), 44AHJD, 68, AC1, AC2, A6"C", A9"C", b581, CA-1, CA-2, CA-3, CA-4, CA-5, D11, L39×35, L54a, M42, N1, N2, N3, N4, N5, N7, N8, N10, N11, N12, N13, N14, N16, Ph6, Ph12, Ph14, UC-18, U4, U15, S1, S2, S3, S4, S5, X2, Z1, φB5-2, φD, ω, 11, (syn=φ11), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A10, A13, b594n, D, M12, N9, N15, P52, P87, S1, S6, Z4, φRE, 3A, 3B, 3C, 6, 7, 16, 21, 42B, 42C, 42E, 44, 47, 47A, 47C, 51, 54, 54×1, 70, 73, 75, 78, 81, 82, 88, 93, 94, 101, 105, 110, 115, 129/16, 174, 594n, 1363/14, 2460 and NN-*Staphylococcus* (1).

Bacteria of the genus *Streptococcus* are infected by the following phage: EJ-1, NN-*Streptococcus* (1), a, C1, FLOThs, H39, Cp-1, Cp-5, Cp-7, Cp-9, Cp-10, AT298, A5, a10/J1, a10/J2, a10/J5, a10/J9, A25, BT11, b6, CA1, c20-1, c20-2, DP-1, Dp-4, DT1, ET42, e10, FA101, FEThs, FK, FKK101, FKL10, FKP74, FK11, FLOThs, FY101, f1, F10, F20140/76, g, GT-234, HB3, (syn=HB-3), HB-623, HB-746, M102, 01205, φO1205, PST, P0, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, Sfi11, (syn=SFi11), (syn=φSFi11), (syn=ΦSfi11), (syn=φSfi11), sfi19, (syn=SFi19), (syn=φSFi19), (syn=φSfi19), Sfi21, (syn=SFi21), (syn=φSFi21), (syn=φSfi21), STG, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φ100, φ101, φ102, φ227, (17201, ω1, ω2, ω3, ω4, ω5, ω6, ω8, ω10, 1, 6, 9, 10F, 12/12, 14, 17SR, 19S, 24, 50/33, 50/34, 55/14, 55/15, 70/35, 70/36, 71/ST15, 71/45, 71/46, 74F, 79137, 79/38, 80/J4, 80/J9, 80/5T16, 80/15, 80/47, 80/48, 101, 103/39, 103/40, 121/41, 121/42, 123/43, 123/44, 124/44, 337/ST17 and NN-*Streptococcus* (34).

Bacteria of the genus *Treponema* are infected by the following phage: NN-*Treponema* (1).

Bacteria of the genus *Vibrio* are infected by the following phage: CTXΦ, fs, (syn=s1), fs2, 1vpfs, Vf12, Vf33, VPIΦ, VSK, v6, 493, CP-T1, ET25, kappa, K139, LaboI) XN-69P, OXN-86, O6N-21P, PB-1, P147, rp-1, SE3, VA-1, (syn=VcA-1), VcA-2, VcA-1, VP1, VP2, VP4, VP7, VP8, VP9, VP10, VP17, VP18, VP19, X29, (syn=29 d'Hérelle), 1, ΦHAWI-1, ΦHAWI-2, ΦHAWI-3, ΦHAWI-4, ΦHAWI-5, ΦHAWI-6, ΦHAWI-7, ΦHAWI-8, ΦHAWI-9, ΦHAWI-10, ΦHC1-1, ΦHC1-2, ΦHC1-3, ΦHC1-4, ΦHC2-1, ΦHC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKW1H-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL-13B-1, ΦPEL13B3-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φ138, 1-11, 5, 13, 14, 16, 24, 32, 493, 6214, 7050, 7227, II, (syn=group 11), (syn=φ2), V, VIII, NN-*Vibrio* (13), KVP20, KVP40, nt-1, O6N-22P, P68, e1, e2, e3, e4, e5, FK, G, J, K, nt-6, N1, N2, N3, N4, N5, O6N-34P, OXN-72P, OXN-85P, OXN-100P, P, Ph-1, PL163/10, Q, S, T, φ92, 1-9, 37, 51, 57, 70A-8, 72A-4, 72A-10, 110A-4, 333, 4996, I, (syn=group I), III, (syn=group III), VI, (syn=A-Saratov), VII, IX, X, NN-*Vibrio* (6), pA1, 7, 7-8, 70A-2, 71A-6, 72A-5, 72A-8, 108A-10, 109A-6, 109A-8, 110A-1, 110A-5, 110A-7, hv-1, OXN-52P, P13, P38, P53, P65, P108, P111, TP1, VP3, VP6, VPI2, VP13, 70A-3, 70A-4, 70A-10, 72A-1, 108A-3, 109-B1, 110A-2, 149, (syn=φ149), IV, (syn=group IV), NN-*Vibrio* (22), VP5, VP11, VP15, VP16, α1, α2, α3a, 3b, 353B and NN-*Vibrio* (7).

Bacteria of the genus *Yersinia* are infected by the following phage: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Hérelle, EV, H, Kotljarova, PTB, R, Y, YerA41, φYerO3-12, 3, 4/C1324-76, 7/F783-76, 903, 1/M6176 and Yer2AT.

In another embodiment, the methods are practiced using a combination of at least 2, at least 3, at least 4, at least 5, at least 6, at least 7, at least 8, at least 9 or a greater number of the aforementioned phages. One skilled in the art recognizes that the efficiency of transformation may be manipulated, e.g., enhanced or suppressed, depending on the particular combination of phages that are employed.

In particular, bacteria species (and corresponding, host-specific bacteriophages) include *Aeromonas hydrophila* (PM2), *Bacillus anthracis* (Gamma), *Bacillus subtilus* (SPP1), *Bordetella pertussis* (See Pereversev et al. *Zh Mikrobiol* 5:54-57, 1981), *Borrelia burgdorferi* (φBB-1, see Eggers et al., *J Bacteriol* 183:4771-4778, 2001), *Brucella abortus* (TB; 212; 371), *Campylobacter jejuni* (φ4, φC), *Clostridium perfringes* (φ3626), *Enterococcus faecalis* (φFC1), *Enterococcus faecium* (ENB6), *Escherichia coli* (P1; T1; T3, T4, T5; T7, KH1, φV10; lambda; φ20; mu), *Klebsiella pneumoniae* (60; 92), *Listeria monocytogenes* (A511, A118; 243; H387; 2389; 2671; 2685; 4211), *Mycobacterium leprae* (mycobacteriophage, L5), *Mycobacterium tuberculosis* (LG; DSGA), *Pseudomonas aeruginosa* (E79, G101; B3; pp. 7), *Salmonella anatum* (E5), *Salmonella bovismorbificans* (98), *Salmonella choleraesuis* (102), *Salmonella enteritidis* (L; P22; 102; FO; IRA; φ8), *Salmonella Newington* (E34), *Salmonella schottmulleri* (31; 102; FO; 14), *Salmonella typhi* (163; 175; ViI; ViVI; 8; 23; 25; 46;

175; FO), *Serratia marcescens* (S24VA), *Shigella dysenteriae* (φ80; P2; 2; 37), *Shigella flexneri* (Sf6), *Staphylococcus aureus* (K; P1; P14; UC18; 15; 17; 29; 42D; 47; 52; 53; 79; 80; 81; 83A; 92; Twort, φ11), *Streptococcus pneumoniae* (Dp-1; Cp-1; HB-3; EJ-1; MM1; VO1), *Streptococcus pyogenes* (φX240; 1A; 1B; T12; 12/12; 113; 120; 124; P58; H4489a), *Vibrio cholerae* (138; 145; 149; 163), and *Yersinia pestis* (A1122; R; Y; P1). Additional information is provided in U.S. Patent Publication No. 2009-0155768.

In particular, Tables 1-3 provide representative examples of particular host-specific phages and the hosts to which they are specific for, including, the receptors through which they mediate their actions. See also Bertozzi et al., *FEMS Microbiology Letters*, 363, 1-11, 2016.

TABLE 1

Receptors in the cell wall of Gram-positive bacteria. Host names are ordered alphabetically.

| Phages | Family | Main host | Receptor(s) |
|---|---|---|---|
| γ | Siphoviridae | *Bacillus anthracis* | Membrane surface-anchored protein phage receptor (GamR) |
| SPP1 | Siphoviridae | *Bacillus subtilis* | Glucosyl residues of poly(glycerophosphate) on WTA |
| φ29 | Podoviridae | *Bacillus subtilis* | Cell WTA (primary receptor) |
| Bam35 | Tectiviridae | *Bacillus thuringiensis* | N-acetyl-muramic acid (MurNAc) |
| LL-H | Siphoviridae | *Lactobacillus delbrueckii* | Glucose moiety of LTA |
| B1 | Siphoviridae | *Lactobacillus plantarum* | Galactose component of the wall |
| B2 | Siphoviridae | *Lactobacillus plantarum* | Glucose substituents in in teichoic acid |
| 5, 13, c2, h, ml3, kh, L | Siphoviridae | *Lactococcus lactis* | Rhamnose moieties in the cell wall |
| φLC3, TP901erm, TP901-1 | Siphoviridae | *Lactococcus lactis* | Cell wall polysaccharides |
| p2 | Siphoviridae | *Lactococcus lactis* | Cell wall saccharides |
| A511 | Myoviridae | *Listeria monocytogenes* | Peptidoglycan (murein) |
| A118 | Siphoviridae | *Listeria monocytogenes* | Glucosaminyl and rhamnosyl components |
| A500 | Siphoviridae | *Listeria monocytogenes* | Glucosaminyl residues |
| φ812, φK | Myoviridae | *Staphylococcus aureus* | Anionic backbone of WTA |
| 52A | Siphoviridae | *Staphylococcus aureus* | O-acetyl group from the 6-position |
| W, φ13, φ47, φ77, φSa2m | Siphoviridae | *Staphylococcus aureus* | N-acetylglucosamine (GlcNAc) glycoepitope |
| φSLT | Siphoviridae | *Staphylococcus aureus* | Poly(glycerophosphate) moiety of LTA |

TABLE 2

Receptors in the cell wall of Gram-negative bacteria. Host names are ordered alphabetically.

| Phages | Family | Main host | Receptor(s) |
|---|---|---|---|
| φCr30 | Myoviridae | *Caulobacter crescentus* | Paracrystalline surface (S) protein |
| 434 | Siphoviridae | *Escherichia coli* | Protein Ib (OmpC) |
| BF23 | Siphoviridae | *Escherichia coli* | Protein BtuB (vitamin B12 receptor) |
| K3 | Myoviridae | *Escherichia coli* | Protein d or 3A (OmpA) with LPS |
| K10 | Siphoviridae | *Escherichia coli* | Outer membrane protein LamB |
| Me1 | Myoviridae | *Escherichia coli* | Protein c (OmpC) |
| Mu G(+) | Myoviridae | *Escherichia coli* | Terminal Glcα-2Glcα1- or GlcNAcα1-2Glcα1- of LPS |
| Mu G(−) | Myoviridae | *Escherichia coli* | Terminal glucose with a β1,3 glycosidic link |
| M1 | Myoviridae | *Escherichia coli* | Protein OmpA |
| Ox2 | Myoviridae | *Escherichia coli* | Protein OmpA |
| ST-1 | Myoviridae | *Escherichia coli* | Terminal Glcα-2Glcα1- or GlcNAcα1-2Glcα1- of LPS |
| TLS | Siphoviridae | *Escherichia coli* | Antibiotic efflux protein TolC |
| TuIa | Myoviridae | *Escherichia coli* | Protein Ia (OmpF) with LPS |
| TuIb | Myoviridae | *Escherichia coli* | Protein Ib (OmpC) with LPS |
| TuII* | Myoviridae | *Escherichia coli* | Protein II* (OmpA) with LPS |
| T1 | Siphoviridae | *Escherichia coli* | Proteins TonA (FhuA) |
| T2 | Myoviridae | *Escherichia coli* | Protein Ia (OmpF) with LPS |
| T3 | Podoviridae | *Escherichia coli* | Glucosyl-α-1,3-glucose terminus of rough LPS |

TABLE 2-continued

Receptors in the cell wall of Gram-negative bacteria. Host names are ordered alphabetically.

| Phages | Family | Main host | Receptor(s) |
|---|---|---|---|
| T4 | Myoviridae | *E. coli* K-12/ *E. coli* B | Protein O-8 (OmpC) with LPS |
| T4 | Myoviridae | *E. coli* B | Glucosyl-α-1,3-glucose terminus of rough LPS |
| T5 | Siphoviridae | *Escherichia coli* | Polymannose sequence in the O-antigen |
| T6 | Myoviridae | *Escherichia coli* | Outer membrane protein Tsx |
| T7 | Podoviridae | *Escherichia coli* | LPS |
| U3 | Microviridae | *Escherichia coli* | Terminal galactose residue in LPS |
| λ | Siphoviridae | *Escherichia coli* | Protein LamB |
| φX174 | Microviridae | *Escherichia coli* | Terminal galactose in rough LPS |
| φ80 | Siphoviridae | *Escherichia coli* | Proteins FhuA and TonB |
| PM2 | Corticoviridae | *Pseudoalteromonas* | Sugar moieties on the cell surface |
| E79 | Myoviridae | *Pseudomonas aeruginosa* | Core polysaccharide of LPS |
| JG004 | Myoviridae | *Pseudomonas aeruginosa* | LPS |
| φCTX | Myoviridae | *Pseudomonas aeruginosa* | Core polysaccharide of LPS |
| φPLS27 | Podoviridae | *Pseudomonas aeruginosa* | Galactosamine-alanine region of LPS |
| φ13 | Cystoviridae | *Pseudomonas syringae* | Truncated O-chain of LPS |
| ES18 | Cystoviridae | *Salmonella* | Protein FhuA |
| Gifsy-1, Gifsy-2 | Siphoviridae | *Salmonella* | Protein OmpC |
| SPC35 | Siphoviridae | *Salmonella* | BtuB (main receptor) and O12-antigen (asssiting receptor) |
| SPN1S, SPN2TCW, SPN4B, SPN13U | Podoviridae | *Salmonella* | O-antigen of LPS |
| SPN6TCW, SPN8TCW, SPN9TCW | Podoviridae | *Salmonella* | O-antigen of LPS |
| SPN7C, SPN9C, SPN10H, SPN12C | Siphoviridae | *Salmonella* | Protein BtuB |
| SPN14, SPN17T, SPN18 | Siphoviridae | *Salmonella* | Protein BtuB |
| vB_SenM-S16 (S16) | Myoviridae | *Salmonella* | Protein OmpC |
| Ω8 | Podoviridae | *Escherichia coli* | α-1,3-mannosyl linkages |
| c341 | Podoviridae | *Salmonella* | O-acetyl group in the mannosylrhamnosyl-O-acetylgalactose |
| P22 | Podoviridae | *Salmonella* | O-acetylgalactose |
| ε34 | Podoviridae | *Salmonella* | [-β-Gal-Man-Rha-] polysaccharide |
| Sf6 | Podoviridae | *Shigella* | Rha II 1-α-3 Rha III linkage |

TABLE 3

Receptors in bacterial complexes other than cell walls. Host names are ordered alphabetically.

| Phages | Family | Main host | Receptor(s) |
|---|---|---|---|
| SPN2T, SPN3C, SPN8T, SPN9T | Siphoviridae | *Salmonella* | Flagellin protein FliC |
| SPN11T, SPN13B, SPN16C | Siphoviridae | *Salmonella* | Flagellin protein FliC |
| SPN4S, SPN5T, SPN6T, SPN19 | Siphoviridae | *Salmonella* | Flagellin proteins FliC or FljB |
| iEPS5 | Siphoviridae | *Salmonella* | Flagellal molecular ruler protein FliK |
| φCbK, φCb13 | Siphoviridae | *Caulobacter crescentus* | Pili portals on the cell pole |
| Fd, Ff, f1, M13 | Inoviridae | *Escherichia coli* | F pilus followed by TolQRA complex in membrane |
| PRD1 | Tectiviridae | *Escherichia coli* | Mating pair formation (Mpf) complex |
| φ6 | Cystoviridae | *Pseudomonas* | Sides of the type IV pilus |
| MPK7 | Podoviridae | *Pseudomonas aeruginosa* | Type IV pili (TFP) |
| MP22 | Siphoviridae | *Pseudomonas aeruginosa* | Type IV pili (TFP) |
| DMS3 | Siphoviridae | *Pseudomonas aeruginosa* | Type IV pili (TFP) |

TABLE 3-continued

Receptors in bacterial complexes other than cell walls. Host names are ordered alphabetically.

| Phages | Family | Main host | Receptor(s) |
|---|---|---|---|
| 29 | Podoviridae | *Escherichia coli* | β-D-glucosido-(1-3)-D-glucoronic acid bonds in capsule |
| K11 | Podoviridae | *Klebsiella* | β-D-glucosyl-(1-3)-β-D-glucuronic acid linkages |
| Vi I | Myoviridae | *Salmonella* | Acetyl groups of the Vi exopolysaccharide capsule |
| Vi II | Siphoviridae | *Salmonella* | Acetyl groups of the Vi exopolysaccharide capsule |
| Vi III, Vi IV, Vi V, Vi VI, Vi VII | Podoviridae | *Salmonella* | Acetyl groups of the Vi exopolysaccharide capsule |

D. Bacteriophage Packaging Sites

A bacteriophage packaging site is a specific DNA sequence on the phage genome for genome packaging into the virion. A plasmid is engineered to contain a phage packaging site so that plasmid is packaged into the transducing particles. Host-specific bacteriophages (and their packaging sites) include but are not limited to SPP1 (SPP1 pac site), P1 (P1 pac site), T1 (T1 pac site), T7 (T7 concatamer junction), lambda (cos site), mu (mu pac site), P22 (P22 pac site), φ8 (φ8 pac site), Sf6 (Sf6 pac site), 149 (149 pac site), and A1122 (A1122-concatamer junction). For most bacteriophages, the packaging site is termed the pac site. In some cases, the packaging site is referred to as a concatamer junction (e.g. T7 concatamer junction). In every case, the packaging site is different from the naturally-occurring adjacent sequences in the bacteriophage genome.

For some bacteriophages, the packaging site may be unknown. In these cases, pac sites can be determined by taking advantage of the property that plasmids containing a functional bacteriophage pac site are packaged. For example, the DNA sequences necessary for packaging of bacteriophage λ, were determined by incorporating small restriction fragments of the λ, phage genomic DNA into a plasmid (Hohn et al., *PNAS USA* 80:7456-7460, 1983). Following introduction into an in vivo packaging strain, the efficiency of packaging/transduction was quantitatively assessed. Using a similar strategy, the pac sites for a number of bacteriophages have been determined: λ, (Miwa et al., *Gene* 20:267-279, 1982); Mu (Croenen et al., *Virology* 144:520-522, 1985); filamentous bacteriophages including fl, fd, M13, and Ike (Russel et al., *J Virol.*, 63:3284-3295, 1989); P22 (Petri et al., *Gene* 88:47-55, 1990; Wu et al., *Mol. Microbiol* 45:1631-1646, 2002); T7 (Chung et al., *J Mol Biol* 216:927-938, 1990), and T3 (Hashimoto et al., *Virology* 187:788-795, 1992).

Embodiments of the methods include bacteriophage packaging sequences and functional fragments thereof. These nucleic acid embodiments can be for example, at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, and 900 nucleotides in length so long as the nucleotide fragment can mediate packaging of plasmid DNA into bacteriophage capsids (as judged by its ability to mediate packaging and thereby produce functional transducing particles). The nucleic acids that comprise the bacteriophage packaging sites or fragments thereof are incorporated into the plasmids.

E. Marker Gene Constructs

Gene technology is widely used to monitor cellular gene expression (Naylor et al., *Biochem Pharm* 58:749-757, 1990). Preferably, the marker molecule is gene which encodes a detectable product, e.g., a protein or enzyme. Particularly preferably, the marker is molecule that is not natively expressed by the phage or the bacteria. For example, the marker may be a heterologous eukaryotic protein, a protein of different bacterial species, or a viral protein.

In one embodiment, the marker is an antigen, an enzyme, an antibody or a fragment thereof, and an aptamer. The term "antigen", as used herein, refers to a molecule that contains one or more epitopes (linear, conformational or both) that promotes specific binding to a binding partner (e.g., an antibody). The term "antigen" can also refer to antibodies, such as anti-idiotype antibodies or fragments thereof, and to synthetic peptide mimotopes that can mimic an antigen or antigenic determinant (epitope). The term "antigen" can also refer to an oligonucleotide or polynucleotide that expresses an antigen or antigenic determinant in vivo. As used herein, the term "epitope" generally refers to the site on an antigen which is recognized by an antibody or a T-cell receptor. It may be a short peptide derived from or as part of a protein antigen. However the term is also intended to include peptides with glycopeptides and carbohydrate epitopes. Several different epitopes may be carried by a single antigenic molecule. The term "epitope" also includes modified sequences of amino acids or carbohydrates which stimulate responses which recognize the whole organism.

In another embodiment, the marker is an antibody. The term "antibody" includes both whole antibody molecules and also antigen-binding fragments thereof. Antibodies include IgG, IgA, IgM, IgE, IgD as well as antibody variants such as single chain antibodies (scFv). Suitable antibody fragments contain an antigen-binding site and thus include but are not limited to Fv, Fab and F(ab)2 fragments. The antibody can be a polyclonal antibody or a monoclonal antibody. In a preferred embodiment, an antibody is a monoclonal antibody. Also included are chimeric or synthetic antibodies. In a particularly preferred embodiment, the antibodies are scFv that bind with specificity to an antigen of interest. The term "specific binding" refers to level of binding of the antibody to a particular target epitope ("signal") over other non-targets ("noise"). Specific detection is achieved when the signal-to-noise for the detection is at least 0.6-fold, 0.7-fold, 0.8-fold, 0.9-fold, 1-fold (100% increase), 1.5-fold, 3-fold, 5-fold, 10-fold, 20-fold, 50-fold, 70-fold, 100-fold, or more. Means for preparing and characterizing antibodies are well known in the art (See, e.g., Lane et al., "*Antibodies: A Laboratory Manual*," Cold Spring Harbor Laboratory, 1988).

In yet another embodiment, the marker is an aptamer. The term "aptamer" used herein refers to single-stranded DNA (ssDNA) or RNA having a high specificity and affinity with respect to a specific material. Immuno-detection methods are costly and slow due to the limitations of the antibody reagents in that they are expensive to manufacture. On the other hand, since the aptamer is synthesized using a relatively simple method, and cells, proteins and small organic materials can be a target material, new detecting methods using the same can be developed, and its specificity and stability are comparable to the developed antibodies. In view of such advantages, DNA aptamers may be used for specific detection of the protein markers. It is generally accepted that an aptamer, which is specific in its binding to a polypeptide, may be synthesized and/or identified by in vitro evolution methods. Means for preparing and characterizing aptamers, including by in vitro evolution methods, are well known in the art (e.g. U.S. Pat. No. 7,939,313).

The present methods comprise, in part, on determining the presence (or absence) or level (e.g., concentration) or activity (e.g., enzyme activity) of at least one marker or indicator in a sample. The term "marker" or "indicator", as it is used herein, refers to a nucleotide sequence that encodes for a nucleic acid (e.g., mRNA), peptide or protein that permits determination or confirmation that the vector has been transfected or transduced correctly, and that its sequences are correctly expressed. The marker may be a nucleotide sequence encoding for a protein or a gene encoding for antibiotic resistance, used to select the cells that carry the vector. As used herein, the term "detecting the presence of at least one marker" includes determining the presence of each marker of interest by using any quantitative or qualitative assay known to one of skill in the art. In certain instances, qualitative assays that determine the presence or absence of a particular trait, variable, genotype, and/or biochemical or serological substance (e.g., protein or antibody) are suitable for detecting each marker of interest. In certain other instances, quantitative assays that determine the presence or absence of DNA, RNA, protein, antibody, or activity are suitable for detecting each marker of interest. As used herein, the term "detecting the level of at least one marker" includes determining the level of each marker of interest by using any direct or indirect quantitative assay known to one of skill in the art. In certain instances, quantitative assays that determine, for example, the relative or absolute amount of DNA, RNA, protein, antibody, or activity are suitable for detecting the level of each marker of interest. One skilled in the art will appreciate that any assay useful for detecting the level of a marker is also useful for detecting the presence or absence of the marker.

In some embodiments, the marker is a reporter molecule that can signify its presence, e.g., via its luminescent properties or its ability to conduct enzymatic reactions. In another embodiment, the marker binds to a reporter molecule to signify the level or activity of the marker. In the latter instance, the reporter may be an antibody or a ligand that binds to a marker protein.

(i) Reporters

In one embodiment, the reporter molecule is a gene, referred to as a reporter gene, that encodes for expression of a detectable protein. Commonly used reporter genes include chloramphenicol acetyltransferase (CAT), 13-galactosidase, luciferase, alkaline phosphatase, and green fluorescent protein (GFP). In general, reporter genes have the advantage of low background activity and sensitive signal detection following gene expression. For example, the development of luciferase and GFP as non-invasive markers of gene expression, combined with ease of detection using sensitive charge-coupled device (CCD) imaging cameras and fluorescence microscopy, has allowed for temporal and spatial information about gene expression even at the single cell level.

A review of luciferase genes and their use as reporter genes provides a list of known luciferase genes, cDNAs, proteins, and corresponding GENBANK Accession numbers for *Vibrio harveyi* (Accession Nos. M10961 and AAA88685), *Vibrio harveyi* (Accession Nos. M10961 and AAA88686), *Vibrio harveyi* (Accession Nos. M28815 and AAA27531), *Vibrio fischeri* (Accession Nos. X06758 and CAA29931) *Vibrio fischeri* (Accession Nos. X06797 and CAA29932), *Vibrio fischeri* (Accession No. AF170104 (including variants thereof)), *Photorhabdus luminescens* (Accession No. M62917), Photinus pyralis (M15077 and AAA29795), *Luciola cruciate* (Accession Nos. M26194 and AAA29135), *Vargula hilgendorfii* (Accession Nos. E02749, M25666, and AAA30332), *Aequorea victoria* (Accession Nos. M16103, AAA27719, M11394, AAA27716, M16104, AAA27717, M16105, AAA27718, L29571, AAA27720, and E02319); *Oplophorus gracilorostris* (Accession Nos. AB030246, BAB13776, AB030245 and BAB13775); *Renilla muelleri* (Accession Nos. AY015988 and AAG54094); and *Renilla reniformis* (Accession Nos. M63501 and AAA29804). See, Greer et al., *Luminescence* 17:43-74, 2002). Greer also provides a large number of constructs and vectors that are useful for imaging (see Table 2, pp 48-52). These vectors are suitable for expression in *Staphylococcus aureus, E. coli* and other bacteria. Among the known luciferases are the prokaryotic luciferases (Lux), and eukaryotic luciferases (Luc, Ruc and their regulatory proteins) both of which are commonly used in imaging of luciferase expression in living cells.

In another embodiment, the reporter molecule comprises a β-galactosidase reporter gene expressed in bacteria (Miller et al., *Experiments in Molecular Genetics*, Cold Spring Harbor Laboratory, Cold Spring Harbor, N.Y.; Sambrook et al., *Molecular Cloning*, Cold Spring Harbor Laboratory, Cold Spring Harbor, N.Y.). β-galactosidase activity expressed by bacterial colonies is detected by blue coloration on medium containing X-Gal (5-bromo-4-chloro-3-indolyl-β-D-galactopyranoside). Chloramphenicol acetyltransferase (CAT) is also suitable for use as a reporter gene in bacteria. CAT is encoded by a bacterial drug-resistance gene (Kondo et al., J Bacteriol 88:1266-1276). It inactivates chloramphenicol by acetylating the drug at one or both of its two hydroxyl groups. In a typical CAT assay, cell extracts are incubated in a reaction mix containing 14C- or 3H-labeled chloramphenicol and n-Butyryl Coenzyme A. CAT transfers the n-butyryl moiety of the cofactor to chloramphenicol. The reaction products are extracted with xylene and the n-butyryl chloramphenicol partitions mainly into the xylene phase, while unmodified chloramphenicol remains predominantly in the aqueous phase. Radiolabeled chloramphenicol that partitions into the xylene phase is measured using a scintillation counter.

Bacterial alkaline phosphatase encoded by phoA of *E. coli* is enzymatically active only when it has been transported across the cellular membrane into the periplasmic space (Gibson et al., Appl and Env Microbiol 68:928-932, 2002). This property has been exploited to engineer PhoA protein as a molecular sensor of subcellular location. Another bacterial alkaline phosphatase (PhoZ) derived from the gram-positive bacterium *Enterococcus faecalis* (Lee et al., J Bacteriol 181:5790-5799, 1999) has been developed as a reporter that is highly active in gram-positive bacteria (Granok et al., J Bacteriol 182:1529-1540, 2000; Lee et al., J Bacteriol 181:5790-5799, 1999). The alkaline phosphatase activity of PhoZ, like that of PhoA, is dependent on its export from the cytoplasm. In an alkaline phosphatase assay, alkaline phosphatase hydrolyzes substrates such as 4-nitrophenyl phosphate (4NPP) to yield a chromogen (e.g. 4-nitrophenol, 4NP).

Reporter genes allow for simpler manipulation procedures (e.g. reduced purification or cell lysis), they are adaptable to large-scale, high throughput screening measurements, and they are compatible with bacteria systems. Reporter genes can be either naturally occurring genes or those produced by genetic manipulation, such as recombinant DNA technology or mutagenesis. Reporter genes are nucleic acid segments that contain a coding region and any associated expression sequences such as a promoter, a translation initiation sequence, and regulatory sequences.

(ii) Bacteria-Specific Promoters

A reporter gene is typically linked to a promoter sequence that controls and directs synthesis of RNA. It will be appreciated by those of ordinary skill in the art that a promoter sequence may be selected from a large number of bacterial genes expressed by various bacterial species. The choice of promoter is made based on the target bacteria to be detected. For a review of strategies for achieving high-level expression of genes in E. coli, see Makrides et al., Microbiol Rev 60:512-538, 1996. An exemplary promoter sequence effective in E. coli is the T7 promoter, but any promoter or enhancer that is functional in prokaryotic cells may be used. Useful promoters include, but are not limited to, lac promoter (E. coli), trp promoter (E. coli), araBAD promoter (E. coli), lac hybrid promoter, (E. coli), trc hybrid prormoter (E. coli), PL (X), SP6, and T7.

A promoter sequence is selected on the basis of its ability to achieve a detectable level of expression in the target pathogenic bacteria. In a preferred embodiment, the reporter gene is preferably coupled to a promoter obtained from the pathogenic bacterial host to be detected. A constitutive promoter will express the reporter at a constant rate regardless of physiological demand or the concentration of a substrate. Alternatively, it may be advantageous to use an inducible promoter to control the timing of reporter gene expression. For inducible promoters such as the lac and trp operons, expression is normally repressed and can be induced at a desired time. In the absence of lactose, the lac promoter is repressed by lac repressor protein. Induction can be achieved by the addition of lactose or IPTG, preventing the binding of repressor to the lac operator. Similarly, the lip promoter is negatively regulated by a tryptophan-repressor complex that binds to the trp operator. For the trp operon, gene expression can be induced by removing tryptophan or by adding β-indoleacrylic acid.

(iii) Bacteria-Specific Origins of Replication

Origins of replication used in the plasmids may be moderate copy number, such as colE1 ori from pBR322 (15-20 copies per cell) or the R6K plasmid (15-20 copies per cell) or they may be high copy number, e.g. pUC oris (500-700 copies per cell), pGEM oris (300-400 copies per cell), pTZ oris (>1000 copies per cell) or pbluescript oris (300-500 copies per cell). The origins of replication may be functional in E. coli or in any other prokaryotic species such as Bacillis anthracis or Yershinia pestis.

Plasmid replication depends on host enzymes and on plasmid encoded and plasmid-controlled cis and trans determinants. For example, some plasmids have determinants that are recognized in almost all gram negative bacteria and act correctly in each host during replication initiation and regulation. Other plasmids possess this ability only in some bacteria (Kues et al., Microbiol Rev 53:491-516, 1989). Plasmids are replicated by three general mechanisms, namely theta type, strand displacement, and rolling circle (reviewed by Del Solar et al. Microbio and Molec Biol Rev 62:434-464, 1998).

For replication by the theta type mechanism, the origin of replication can be defined as (i) the minimal cis-acting region that can support autonomous replication of the plasmid, (ii) the region where DNA strands are melted to initiate the replication process, or (iii) the base(s) at which leading-strand synthesis starts. Replication origins contain sites that are required for interactions of plasmid and/or host encoded proteins. Plasmids undergoing theta type replication also include pPS10, RK2 (containing oriV), RP4, R6K (containing oriy), ColE1 and ColE2. ColE1 is the prototype of a class of small multicopy plasmids that replicate by a theta-type mechanism. The origin of C61E1 replication spans a region of about 1 kb (Del Solar et al. 1998).

Examples of plasmids replicating by the strand displacement mechanism are the promiscuous plasmids of the IncQ family, whose prototype is RSF1010. Members of this family require three plasmid-encoded proteins for initiation of DNA replication. These proteins promote initiation at a complex origin region, and replication proceeds in either direction by a strand displacement mechanism. The origin of replication has been defined as the minimal region able to support bidirectional replication when the RSF110 replication proteins (RepA, RepB, and RepC) are supplied in trans by a second plasmid. The minimal ori region includes three identical 20-bp iterons plus a 174 bp region that contains a GC-rich stretch (28 bp) and an AT-rich segment (31 bp) (Del Solar et al. 1998).

Replication by the rolling circle (RC) mechanism is unidirectional, and is considered to be an asymmetric process because synthesis of the leading strand and synthesis of the lagging strand are uncoupled. Studies on the molecular mechanisms underlying RC replication have been done mainly with the staphylococcal plasmids pT181, pC221, pUB110, pC194, and with the streptococcal plasmid pMV158 and its Amob derivative pLS1. Other plasmids or phages that undergo RC replication include but are not limited to pS194, fd, φX174, pE194 and pFX2 (Del Solar et al. 1998).

Prokaryotes have a circular molecule of chromosomal DNA, typically with a single origin of replication. For example, the chromosomal origin of replication of E. coli and other bacteria is termed oniC. The present methods envision the use of origins of replication known in the art that have been identified from species-specific plasmid DNAs (e.g. ColE1, R1, pT181, and the like discussed herein above), from bacteriophages (e.g. φX174 and M13) and from bacterial chromosomal origins of replication (e.g. oriC).

(iv) Antibiotic Resistance Genes

The plasmid DNA of the transducing particles will optionally have an antibiotic resistance gene to facilitate molecular biology cloning of the plasmid and to allow for selection of bacteria transformed by plasmid. Antibiotic resistance genes are well known in the art and include but are not limited to ampicillin resistance (Ampr), chloramphenicol resistance (Cmr), tetracycline resistance (Tetr), kanamycin resistance (Kanr), hygromycin resistance (hyg or hph genes), and zeomycin resistance (Zeor). Preferably, the antibiotic resistant gene protects the bacteria from the antimicrobial or cytotoxic effect of a drug other than (or different from) the drug whose resistance or susceptibility is being tested. In another embodiment, the antibiotic resistant gene protects the bacteria from the antimicrobial or cytotoxic effect of a drug which is the same as the drug whose resistance or susceptibility is being tested.

F. Methods of Making Transducing Particles

The transducing particles or recombinant phages used in the present methods are obtained by modifying a naturally-occurring bacteriophage to carry a gene capable of transforming the target bacteria to an easily recognizable phenotype, referred to hereinafter as the reporter gene. The transducing particle must be capable of specifically introducing the reporter gene into the target bacterial host in such a way that the bacterial host can express the gene function in a detectable manner. A large number of bacteriophages exist and may be selected for modification based on the desired host range and the ability of the bacteriophage to carry and transduce the gene of interest. In particular, the bacteriophage must be large enough to accommodate the reporter gene, the associated promoter region, the phage packaging site and any other DNA regions which may be included. Modified bacteriophages will usually retain the normal host range specificity of the unmodified bacteriophage, although some alteration in specificity would be acceptable so long as it does not affect the ability to identify the selected target bacteria.

The bacteriophages to be modified may be temperate or virulent, preferably being temperate. Modification of the bacteriophage results in a transducing particle that remains capable of introducing the reporter gene into a target bacterial host. The reporter gene is part of a plasmid or other self-replicating episomal unit which will be sustained and expressed in the infected host.

Transduction of the reporter gene may take place via transient expression (i.e., expression from a reporter gene which is not stably inherited by the cell) of the reporter gene. In such case, the DNA transduced by the bacteriophage may not survive intact through the entire test period. However, transcription of the reporter gene transduced by the phage will be sufficiently efficient before the DNA is degraded to ensure that the bacteria has assembled a functional reporter gene by the end of the test period. The bacteria can thus be detected by the assay even if the bacteria degrade the phage DNA.

Bacteriophages useful in the present methods may be obtained from microbiological repositories, such as the American Type Culture Collection, P.O. Box 1549, Manassas, Va., 20108, USA. Virulent bacteriophages are available as bacteria-free lysates, while lysogenic bacteriophages are generally available as infected host cells. Wild-type bacteriophage obtained from any source may be modified by conventional recombinant DNA techniques in order to introduce a desired reporter gene capable of producing the detectable phenotype of interest. Prior to introduction, the reporter gene of interest will be combined with a promoter region on a suitable gene cassette. The gene cassette may be constructed by conventional recombinant DNA techniques in a suitable host, such as E. coli. Both the reporter gene and the promoter region should be chosen to function in the target host, and the cassette may optionally include a second reporter gene, such as antibiotic resistance, heavy metal resistance, or the like, to facilitate in vitro manipulation.

The reporter gene (or genes, if not a single gene system) are capable of expressing a screenable phenotype in the target bacterial host. As used hereinafter, the phrase screenable phenotype is intended to mean a characteristic or trait which allows cells that express the phenotype to be distinguished from other cells which do not express the phenotype, even when all cells are growing and reproducing normally in a mixed culture. That is, detection of the characteristic or trait may be carried out while the infected target cells are present in mixed population of viable, usually proliferating non-target bacteria which do not express the phenotype. Preferably, the screenable phenotype will comprise a visually detectable trait, i.e., one that can be directly or indirectly observed in a mixed population of target and non-target cells. The phenotype will usually not be selectable, i.e., one which provides for survival or preferential growth under particular conditions (positive selection) or which provides for growth inhibition or killing under particular conditions. The method does not require that target bacteria present in the sample be isolated from or enriched relative to non-target bacteria which may be present in the sample because the trait will be observable when target bacteria comprise only a portion of the viable bacteria present.

The reporter gene can encode the screenable phenotype by itself or may be part of a multiple gene system encoding the phenotype, where other genes are present in or separately introduced to the host to be detected. For example, the transducing particle may carry the lacZα gene which requires a complementary lacZβ gene or lacZΔM15 deletion in the host for expression.

Suitable screenable phenotypes include bioluminescence, fluorescence, enzyme-catalyzed color production (e.g., using the enzyme alkaline phosphatase), and the like. Each of these phenotypes may be observed by conventional visualization techniques which provide the chemical reagents necessary to complete a signal producing reaction. Preferred is the use of immunodetection, and more particularly a lateral flow immunoassay for detecting a heterologous enzyme or protein or for detecting a molecule that is co-expressed with an enzyme or protein where the co-expressed molecule serves as indicator of a functioning expression system.

For the bacteriophage, it is possible to package the plasmid or the reporter gene cassette by attachment of the bacteriophage packaging site in a DNA construct with the plasmid or cassette. The packaging site may be obtained from the bacteriophage genome and cloned into the plasmid carrying the reporter gene, promoter region, and optional second reporter. The plasmid may then be transferred to a suitable bacterial host. The bacterial host will then produce transducing particles having the plasmid and/or marker gene cassette packaged within a bacteriophage coat capable of inserting the plasmid DNA into bacteria of its host range. The plasmid is transposed into the desired bacteriophage by simultaneous infection of a suitable host with both the plasmid and the bacteriophage. The host cells are incubated and the transducing particles are collected. A fraction of the phage will be carrying the plasmid. The transducing particles can be separated from the phage by conventional techniques.

The host-specific bacteriophage packaging sites are substantially isolated from sequences naturally occurring adjacent thereto in the bacteriophage genome. As used herein, the term "substantially isolated" with respect to bacteriophage packaging sites, means they that are not in their natural environment. That is, the packaging sites are not in a full-length, bacteriophage genomic nucleic acid sequence found in nature. The packaging sites may be isolated from the full length bacteriophage genomic sequence via experimental techniques, such as use of restriction endonuclease enzymes and cloning or amplification by the polymerase chain reaction. The packaging sites also may be produced synthetically.

A bacteriophage packaging site is a nucleic acid fragment devoid, in whole or part, of sequences normally associated with it in nature; or a sequence, as it exists in nature, but having heterologous sequences in association therewith. It is a fragment disassociated from the phage genome.

As used herein, the phrase "functional equivalents" in the context of bacteriophage packaging sites means packaging sites that function the same, qualitatively, as the wild type bacteriophage packaging sites. Thus, if an isolated bacteriophage packaging site directs packaging of DNA, a DNA fragment would be a functional equivalent if it also directs packaging of DNA in the same manner. Quantitative equivalence is not needed for a fragment to be a functional equivalent according to the method. Thus bacteriophage packaging sites that have nucleotide substitutions, deletions and/or additions can be functional equivalents of an isolated bacteriophage packaging site.

G. Methods of Using Bacteriophages

The aforementioned embodiments may be practiced using transducing phage particles made up of fully intact phages or variants thereof comprising minimal structural elements to allow transduction of the particles into host cells. In some instances it will be possible to infect a biological sample and observe the alteration and phenotype directly, although in other cases it may be preferred to first prepare a mass culture of the bacteria present in the sample. Methods for obtaining samples and (if necessary) preparing mass culture will vary depending on the nature of the biological sample, and suitable techniques for preparing various sample types are described in detail in standard microbiology and bacteriology texts such as Bergey's *Manual of Determinative Bacteriology* ($8^{th}$ ed.), Buchanan and Gibbons (eds.) Williams & Wilkens Co., Baltimore (1974); *Manual of Methods for General Bacteriology*, Gerhardt et al. (eds.), Am. Soc. Microbiology, Wash. (1981); and Manual of Clinical Microbiology (8th ed.), Patrick, R et al. (eds.), Am. Soc. Microbiology, Washington (2003).

The phage itself may be added to the sample in a variety of forms. It may be added in a dry state. The phage may be mixed or suspended into a liquid reagent mixture. It may be suspended in a vial to which the sample is added. It also may take any other suitable form. The phage added to the sample is sometimes herein referred to as "the parent phage." Once contacted with bacteriophage, the sample is referred to as a phage exposed sample.

The phage exposed sample may be incubated for a predetermined time. Incubation may be for a sufficient time to allow production of the phage marker in infected target bacteria if present in the exposed sample. The phage exposed sample is in a condition that is conducive to phage infection of the target bacteria. This can be accomplished in a variety of ways. For example, the parent phage may be mixed into a reagent that, when added to the sample, results in a test sample conducive to infection. The sample may be prepared in many different ways to establish conditions conducive to phage infection.

Assuming there were target bacteria in the sample, the test sample will contain a phage marker. The parent phage infects the target bacteria by attaching themselves to cell walls of the target bacteria and injecting the viral nucleic acid to create infected bacteria. The recombinant bacteriophage marker gene is then abundantly expressed in the infected bacteria. If the bacteria are metabolically active, e.g., growing or dividing, then each progeny will contain additional copies of the marker gene (or be infected by the phage), thus, generating larger signals. In contrast, if the bacteria are quiescent or dead, then smaller signals are generated.

The marker may be analyzed via implementation of a plurality of processing steps. In one embodiment, the method involves lysing bacteria. In one embodiment, a microbial lysozyme is added to the bacteriophage exposed sample. In one embodiment, lysing involves adding chloroform to the bacteriophage exposed sample, treating the bacteriophage exposed sample with acid, or otherwise physically processing the bacteriophage exposed sample.

In contrast to other methods, production of progeny phage, rupturing of the host, release of progeny phage into the test sample and subsequent rounds of bacterial infection are not required. Moreover, while many prior art methods rely on detecting intact progeny phages, an embodiment of the present disclosure involves the detection of an overexpressed marker protein, which is not natively expressed by the bacteria or the phage or bacteria-infected host such as human. In other embodiments, the product of the marker gene may confer certain phenotype, e.g., antibiotic resistance or enhanced growth property, which may be functionally screened.

In one embodiment, the bacteriophage marker is an indirect indicator of the presence of target bacteria in the sample. Where the bacteriophage marker is a component of parent phage, the initial concentration of parent phage in the exposed sample may be controlled such that the background signal produced is undetectable in the assay. Thus, if no target bacteria are present in the sample, no infection occurs, no recombinant bacteriophage marker gene is expressed, and no new bacteriophage marker is synthesized. In one embodiment, a negative control is run using a control sample that is known to lack the target bacterial type in order to confirm that the bacteriophage used does not produce a background signal in the assay. Other aspects of the disclosure may provide for use of a negative control to identify a background signal that is distinguishable from any signal arising from an exposed sample comprising target bacteria.

In certain embodiments, once the biological sample has been prepared (with or without growth of a mass culture), it will typically be exposed to transducing particles under conditions which promote binding of the particles to the bacteria and injection of the genetic material, typically at a temperature which supports rapid growth of the bacteria (e.g., 35° C. to 40° C.) without agitation for a time sufficient to allow infection (e.g., 15 minutes to 120 minutes). Following infection, the cells are incubated to allow expression of the reporter gene and reporter gene expression is detected as described below.

The methods are applicable for homogenous isolates as well as heterogeneous bacterial samples, comprising, e.g., a plurality of species of bacteria. The term "plurality" means two or more units, e.g., species of bacteria, although the individual units need not be structurally and/or functionally different. In certain embodiments, the samples may be screened to provide a homogeneous bacterial population, e.g., using a particular nutritional media that is adapted to the particular population.

In contrast to conventional phage transduction techniques intended to produce homogeneous colonies of transduced bacterial cells, the methods do not require that the transduced bacteria be isolated in any way. Instead, the screenable phenotype, e.g., a visually observable trait, conferred by the reporter gene or a product thereof, can be detected in a non-selected portion of the biological sample where viable, usually proliferating, non-target bacteria will be present. The screening can occur without selection since there is no need to isolate the transduced bacteria.

In some embodiments, the method comprises analyzing a sample for the presence or absence of the marker nucleic acid or a product thereof. Suitable methods for the detection of marker nucleic acids or products thereof are known in the art, and can and will vary depending upon the nature of the sample.

In some embodiments, methods for determining susceptibility or resistance of bacteria to an antibiotic are provided, by carrying out the aforementioned antibiotic treatment, phage transformation and detection steps. These steps of antibiotic treatment and phage transformation may be carried out in any order or simultaneously. In one embodiment, the steps of antibiotic treatment and phage transformation are conducted sequentially. The term "sequentially" as used herein means that the steps are carried out in sequence, for example at an interval or intervals of minutes, hours, days or weeks. If appropriate the steps may be carried out in a regular repeating cycle. In another embodiment, the antibiotic treatment and phage transformation steps are carried out together, followed by the determination steps.

H. Detection Methods

Methods of detecting a reporter gene or a product thereof may be indirect or direct. Indirect detection may comprise separating the reporter gene or a product thereof from other components in the sample, or concentrating reporter gene or a product thereof in the sample, followed by detection of reporter gene or a product thereof in the purified or concentrated sample. The reporter gene or product thereof may be detected in the liberated state (e.g., in the media containing phages) or in the bound form (e.g., contained inside bacteria either in the cytosol or integrated into the genome). In some instance, the reporter is a molecule that is expressed on the surface of the bacteria, which allows detection thereof without the need for lysis. In other embodiments, the reporter may be a protein having enzymatic activity, e.g., CAT activity or AP activity, as described previously. In such instances, the reporter activity is determined using enzymatic techniques. In yet another embodiment, the reporter may be a protein displaying antigenicity to a known antibody or a binding partner of a known aptamer or protein.

In preferred embodiments, the reporter gene or a product thereof is detected directly by detecting the presence of the protein product of the gene or a fragment of the protein (e.g., a peptide containing antigenic determinants to which an antibody binds specifically thereto). In this regard, an epitope binding agent such as an antibody, aptamer, or other molecular ligand that recognizes the reporter protein or a fragment thereof may be used to detect reporter protein or a fragment thereof. In an exemplary embodiment, an antibody or an antigen-binding fragment thereof is used to detect the presence of reporter protein or a fragment thereof. In other embodiments, an antibody may be used to detect products that are generated from the biosynthetic activity of the reporter protein, e.g., wherein the reporter is a protease that has specific activity against another protein, the digestion product of the second protein is detected.

In one embodiment, the reporter protein or a fragment thereof is detected using mass spectrometry. In particular, techniques linking a chromatographic step with a mass spectrometry step may be used. Generally speaking, the presence of reporter protein or a fragment thereof may be determined utilizing liquid chromatography followed by mass spectrometry.

In some embodiments, the liquid chromatography is high performance liquid chromatography (HPLC). Non-limiting examples of HPLC may include partition chromatography, normal phase chromatography, displacement chromatography, reverse phase chromatography, size exclusion chromatography, ion exchange chromatography, bioaffinity chromatography, aqueous normal phase chromatography or ultrafast liquid chromatography. In one embodiment, the liquid chromatography may be ultrafast liquid chromatography.

In some embodiments, the mass spectrometry may be constant neutral loss mass spectrometry. In other embodiments, the mass spectrometry may be tandem mass spectrometry (MS/MS). In a different embodiment, the mass spectrometry may be matrix-assisted laser desorption/ionization (MALDI). In a specific embodiment, the mass spectrometry may be electrospray ionization mass spectrometry (ESI-MS).

In an exemplary embodiment, the method comprises liquid chromatography followed by tandem mass spectrometry. In a particularly exemplary embodiment, the method comprises liquid chromatography followed by tandem mass spectrometry as described in the examples. In another exemplary embodiment, the method comprises liquid chromatography followed by constant neutral loss mass spectrometry. In a particularly exemplary embodiment, the method comprises liquid chromatography followed by constant neutral loss mass spectrometry as described in the examples. In still another exemplary embodiment, the method comprises liquid chromatography followed by electrospray ionization mass spectrometry (ESI-MS).

In each of the above embodiments, the liquid chromatography followed by mass spectrometry may be used to determine the presence of the reporter protein or a fragment thereof in a sample, or the liquid chromatography followed by mass spectrometry may be used to determine the presence and quantity of the reporter protein or a fragment thereof in a sample. In preferred embodiments, the liquid chromatography followed by mass spectrometry may be used to determine the presence of the reporter protein or a fragment thereof in a sample.

In general, an epitope binding agent-based method of assessing the presence or an amount of the reporter protein or a fragment thereof comprises contacting a sample comprising the reporter protein or a fragment thereof with an epitope binding agent specific for the reporter protein or a fragment thereof under conditions effective to allow for formation of a complex between the epitope binding agent and the reporter protein or a fragment thereof. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett et al., *Xenobiotica* 30(2):155-177, 2000).

In order to allow a complex to form between the epitope binding agent and the reporter protein or a fragment thereof, the individual components are incubated under effective conditions for a period of time long enough for the epitope binding agent to bind to any antigen present. After this time, the complex may be washed to remove/reduce non-specific binding and the complex may be detected by any method well known in the art. Methods of detecting the complex between the epitope binding agent and the reporter protein or a fragment thereof are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, streptavidin, protein A, protein G, antibodies or fragments thereof, polyhistidine, Ni2+, Flag tags, myc tags, heavy metals, and enzymes (including alkaline phosphatase, peroxidase, and luciferase). Such methods are well-known in the art.

In some embodiments, the complexes are detected via an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an epitope binding agent, such as an antibody. Unbound analyte is washed away and the bound analyte is measured. In an alternative embodiment of a competitive immunoassay, an unlabeled analyte in a sample displaces labeled epitope binding agent, such as an antibody, from immobilized analyte. The amount of displaced antibody is measured as an indication of the amount of analyte in the sample. In a non-competitive immunoassay, the epitope binding agent, such as the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In different embodiments, the epitope binding agent-based method is immunohistochemistry (IHC). In alternative embodiments, the epitope binding agent-based method is an array. In different embodiments, the epitope binding agent-based method is a lateral flow assay. A lateral flow assay may be a device intended to detect the presence (or absence) of a target analyte in sample.

A second approach for increasing the ability to specifically identify bacterial hosts involves the use of immunoadsorption. Immobilized antibodies, including antisera or monoclonal antibodies, are utilized to specifically capture bacterial cells based on the identity of their cell surface epitopes. The bacteria may then be further detected using the transducing particles, as described above. Suitable materials and methods for the immunoadsorption of particular bacterial species and strains on solid phase surfaces are described in Enterobacterial Surface Antigens: Methods for Molecular Characterization, Korhonen et al. (eds.), Elsevier Science Publishers, Amsterdam (1986).

In another embodiment, the reporter protein or a fragment thereof may be detected using cytometric techniques. Although methods for conducting cytometric measurements of cultured bacteria have been reported elsewhere (Martinez et al., *Cytometry* (1982) 3(2):129-33; Suller et al., *J Antimicrob Chemother* (1997) 40(1):77-83; and Roth et al., *Appl Environ Microbiol* (1997) 63(6):2421-31), they do not involve detection of phage reporter proteins. The cytometric detection methods can be adapted for both Gram-positive and Gram-negative bacteria, e.g., *Escherichia coli* (Martinez, supra), *Bacillus cereus* (Roth, supra), *S. aureus* (Suller et al., *J Antimicrob Chemother* (1997) 40(1):77-83), *Staphylococcus epidermidis* (Cohen et al., *J Clin Microbiol* (1989) 27(6):1250-6), *Streptococcus pyogenes* (Cohen, supra), *Klebsiella pneumoniae* (Cohen, supra), *Pseudomonas aeruginosa* (Cohen, supra), *P. stutzeri* (Cohen, supra), *Proteus mirabilis* (Cohen, supra), and *Enterobacter* spp. (Cohen, supra).

In the aforementioned embodiments, the method makes use of host-specific recombinant or engineered phages. For example, a genetically modified φA1122 capable of infecting *Yersinia pestis* can be used for specific detection of *Yersinia pestis*. To detect multiple target bacterial types, one species of bacteriophage specific to each target bacterial type may be added to a single test sample, or individually to divisions thereof.

FIG. 1 shows an exemplary workflow according to one embodiment of a method described herein. A sample 10 comprising a bacteria is obtained. As described above, the sample can be from a subject, from a food item, from the environment, etc. The sample can be processed or treated, if needed or desired. An aliquot of the sample is incubated or cultured 12 in the presence of an antibiotic and, optionally, an aliquot of the sample is incubated or cultured in the absence of the antibiotic. Simultaneously or sequentially, the sample aliquots are incubated or cultured 12 with a recombinant or engineered phage specific for the bacteria in the sample. As described above, the engineered phage comprises a heterologous marker. Then the cultures generated by incubation with the antibiotic and the engineered phage are analyzed 14 to determine presence or absence (quantative or qualitative) of the marker and the result or data 16 is reported.

FIG. 2 shows an exemplary workflow according to another embodiment of a method described herein. A sample 20 comprising a bacteria is obtained. The sample can be processed or treated, if needed or desired. Containers 22 are prepared that contain a fluid medium with and without an antibiotic. Aliquots of sample 24 are placed into each container, and mixed 26. Then, each container is incubated for a desired time at a desired temperature, and in this embodiment, each container is incubated for 2 hours at 35° C. (28). The container can be mixed again after incubation, and then the engineered phage is introduced into the container, mixed (34), and then incubated (36) to generate a secondary culture. An aliquot of the secondary culture is deposited onto a lateral flow immunoassay device (38) which is then analyzed (40) for the presence or absence (quantative or qualitative) of the heterologous marker.

The workflow of FIGS. 1 and 2 are exemplary for conducing the methods and assays described herein to screen candidate antibiotics for efficacy against a bacterial sample, a bacterial strain or a mix of bacterial strains. Generally, the method comprises contacting a bacterial sample with a test antibiotic to obtain a primary culture and with a vehicle lacking the test antibiotic to obtain a control primary culture; contacting a specific bacteriophage comprising a nucleic acid sequence that encodes for expression of a heterologous reporter gene with the primary culture and with the control primary culture, to obtain a first secondary culture that comprises bacteria treated with the test antibiotic(s) and a second secondary culture that comprises bacteria not treated with the test antibiotic(s); and detecting a level or activity of the reporter gene or a product thereof in the first and second secondary cultures, wherein a reduction (or absence) in the level or activity of the reporter gene or a product thereof in the first secondary culture compared to the second secondary culture indicates that the test compound is an antibiotic agent. The methods are also used for screening a single test antibiotic against a plurality of bacterial strains. The methods are also used for the minimum inhibitory concentration (MIC) of an antibiotic or candidate antibiotic and/or screening to determine the efficacy of a clinical antibiotic compound.

As used herein, the term "minimum inhibitory concentration" refers to the lowest concentration of an antibiotic that will inhibit the visible growth of a microorganism. The term also encompasses the lowest concentration of an antibiotic that effects bacterial cell death or inhibits cell wall repair using the methods and assays described herein. In one embodiment, the methods and assays described herein permit the determination of a minimum inhibitory concentration for an antibiotic or candidate antibiotic against a bacterial strain. In one embodiment, the minimum inhibitory concentration of an antibiotic can be determined by measuring a modulation in the response of the bacterial cells (e.g., uptake or extrusion of a reporter stain, change in morphology, change in metabolism, etc.) in a sample exposed to an antibiotic compared to the same bacterial cells in a sample not exposed to the antibiotic or in a sample exposed to different concentrations of the same antibiotic.

The minimum inhibitory concentration is a clinically relevant value indicating the minimum effective dose of an antibiotic to be administered to a subject to induce bacterial cell death and/or reduce at least one symptom of the bacterial-mediated disease. Clinically, the minimum inhibitory concentrations are used not only to determine the amount of antibiotic that a subject will receive but also to determine the preferred antibiotic to be used. A minimum inhibitory concentration can also be determined for a candidate antibiotic to permit e.g., efficacy determination and dosing information for clinical trials.

The present methods are useful in patient diagnosis as they permit determination of bacterial sensitivity to antibiotics and other bactericides. By performing a short incubation of the bacteria with an antibiotic or bactericide to be screened prior to exposure to the transducing particles, the metabolic activities of the cells will be halted and the alteration of the phenotype prevented. Such testing will be useful after the presence of the bacteria is initially confirmed using the transducing particles as described above. Antibiotics and bactericides which are determined to be lethal to the bacterial infection may then be employed for treatment of the subject. Such rapid and early detection of useful antibiotics and bactericides can be invaluable in treating severe bacterial infections.

In one embodiment, the diagnostic method may involve contacting a sample of a subject suffering from or suspected to be at risk of a bacterial disease with one or more recombinant phages as described herein; detecting and optionally quantitating the presence or absence of the marker expressed by the phage; correlating the presence of the marker to an etiological agent of the bacterial disease (e.g., *S. aureus*), thereby diagnosing the bacterial disease in the subject. By "subject" is meant any member of the phylum Chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term covers both adult and newborn individuals.

In certain embodiments, after a positive diagnosis of the bacterial disease is made, the subject may be optionally treated, managed, and followed-up in line with standard clinical procedures. For instance, a subject may be treated with an effective amount of a pharmaceutical agent, e.g., an antibiotic. For purposes of the present methods, an "effective amount" of an agent will be that amount which generates a response against the etiological agent, e.g., *S. aureus*, in a subject. In this regard, a subject suffering from pharyngitis may be treated with penicillin G benzathine and/or amoxicillin. If the subject is found to not respond to the treatment, the etiological agent may be analyzed for antibiotic resistance using the methods described above. If a positive identification as to the resistant strain is made, then the subject may be treated with a second antibiotic agent or a higher dosage of the antibiotic agent, or a combination of two or more antibiotic agents.

Similarly, the present methods are useful in detecting the presence of antibiotics, e.g., antibiotic residues in animal products. In this approach, an extract of the material to be analyzed is added to a culture of a bacterial strain sensitive to the antibiotic in question, and the mixture is incubated for a period predetermined to be sufficient to kill the strain if a given amount of antibiotic is present. At this point, transducing particles specific to the strain are added, and the assay as described herein is performed. If the given amount of antibiotic is present, the cells of the bacterial strain will be dead and the read-out will be negative (i.e., lack of luminescence in a luciferase assay). If the given amount of antibiotic is not present or lower than MIC, then bacteria will survive and the read-out will be positive (i.e., luminescence).

In a specific embodiment, a means is provided for assaying bacteria which have been previously rendered susceptible to transducing particles on a phage-specific basis. That is, in a first step, the target bacteria are modified, e.g., by transformation, so that they contain or express a cell-specific receptor for the bacteriophage of interest. In a second step, the modified (or tagged) bacteria are introduced into, or mixed into, a sample environment in which they are to be followed. The sample environment can be any setting where bacteria exist, including outdoors (e.g., soil, air or water); on living hosts (e.g., plants, animals, insects); on equipment (e.g., manufacturing, processing or packaging equipment); and in clinical samples. The bacteriophage assay as described herein is then conducted using bacteriophage specific for the introduced receptor, and the presence of the tagged bacteria can be monitored or quantified.

The aforementioned embodiments are further described in view of the following non-limiting examples.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1

Construction of Recombinant Bacteriophage for Expression of Heterologous Marker

In this study, a molecule (marker) that is not naturally produced by target cells or by the phage vector or by the bacterium-infected host is prepared, followed by specific detection of the heterologous molecule (marker) by immunoassay. The marker molecule can be a peptide or a protein that is optionally tagged, e.g., with a polyhistidine (His) tag, etc.

Construction of a Recombinant Bacteriophage:

A recombinant bacteriophage is constructed by inserting a DNA sequence encoding for the heterologous marker into a strongly expressed region of the phage genome downstream of the nucleic acid sequence encoding the capsid protein (cps) via homologous recombination mediated by a recombinant plasmid. A strong promoter, located upstream of cps, is selectively activated in the course of the expression of the bacteriophage genome following infection, producing many copies of the corresponding mRNA transcripts. Construction of the recombinant bacteriophage is accomplished using a fusion product of the nucleic acid encoding a reporter, having suitable translation signals (ribosome binding site, intermediate region, start codon). A representative method is described in Loessner et al., *Appl. Environ. Microbiol.*, 62(4):1133-40, 1996 and U.S. Pat. No. 5,824, 468.

Electro-Transformation of the Plasmid Vector into an Electrocompetent *E. coli* K1 Strain (ATCC Strain 23503):

The strain is made electrocompetent by growing to an optical density (OD) of 0.8 at 37° C. in Luria-Bertani (LB) broth, followed by several washes in 15% glycerol. Electrotransformation is accomplished with a GENE PULSER available from Bio-Rad Labs (Hercules, Calif.).

Infection of the Transformed *E. coli* K1 Strain with Native Type Bacteriophage:

After infection of the host bacteria, at least a small number of the native bacteriophage will undergo homologous recombination with the portions of the capsid sequence flanking luxAB in the plasmid, thus transferring the luxAB to form recombinant phages. The transformed bacteria are grown to an OD of 0.4 at 37° C. in LB-ampicillin media. Bacteriophage K1-5 is added at a multiplicity of infection (MOI) of approximately 1 bacteriophage per 10 bacteria, and the OD is monitored until lysis occurs. The lysate is collected by filtering through a 0.45 micron nitrocellulose membrane (available from Millipore Corp., Bedford, Mass.).

The lysate is plated and plaqued, using a serial dilution, onto wild type *E. coli* K1 (ATCC 23503) growing on LB solid agar with 50 µg per mL ampicillin and screened for recombinant K1-5 bacteriophage by assaying plaques for reporter activity. Confirmation that the recombinant bacteriophage has been generated containing the properly-integrated reporter gene sequence can be conducted by sequencing the phage genome. Sequencing is accomplished with the aid of a commercial sequencer (Commonwealth Biotechnologies, Richmond, Va.).

Finally, the expressed marker is detected by immunoassay.

Example 2

Creation of Recombinant Bacteriophages Using DNA Transposition

A bacteriophage containing a heterologous reporter nucleic acid is constructed using the commercially available EZ::TN™ transposase system (Epicenter Technologies, Madison, Wis.) as described in Goryshin et al., *J. Biol. Chem.*, 273(13):7367-7374, 1998. Then, the terminally ME-bound EZ::TN™ transposome is electrotransformed into an electrocompetent *E. coli* K1 strain (ATCC strain 23503). The strain is made electrocompetent by growing to an optical density (OD) of 0.8 at 37° C. in LB media, followed by several washes in 15% glycerol. Electrotransformation is accomplished using the BIORAD GENE PULSER available from Bio-Rad Laboratories (Hercules, Calif.).

The transformed *E. coli* K1 strain is infected with native type K1-5 bacteriophage. The transformed bacteria are grown to an OD of 0.4 at 37° C. in LB-ampicillin media. Bacteriophage K1-5 is added at a multiplicity of infection of approximately 1 bacteriophage per 10 bacteria, and the OD is monitored until lysis occurs. After infection of the transposome-electrotransformed host bacteria, at least a small number of the native K1-5 bacteriophage will receive the heterologous reporter gene by random transposition at an innocuous position that does not affect the plaque-forming ability of the phage. The lysate is collected by filtering through a 0.45 micron nitrocellulose membrane (available from Millipore Corp., Bedford, Mass.).

The lysate is screened for activity of the product of the reporter gene using standard methods, e.g., immunoassay for the reporter protein using an antibody or a fragment that specifically binds to the reporter protein. The primary antibody may be detected with a secondary antibody containing a detectable moiety.

Example 3

Screening Samples Obtained from a Subject Using Recombinant Bacteriophage

A subject (e.g., a human patient) exhibiting symptoms of bacterial infection (for example, fever, headache, abdominal pain, and nausea) is identified, and the following samples are collected from the subject: a 0.01 mL cerebrospinal fluid (CSF) sample, a 1.0 mL sputum sample, and a 1.0 mL blood sample. Each sample is diluted with 4.0 mL of LB broth, thus promoting growth of all bacteria present in the respective sample, and is incubated at 37° C. for 4 hours. After incubation, each sample is distributed by 100 µL aliquots into 30 wells of a 96-well plate. Aliquots of the blood sample are added to wells 1-30, aliquots of the CSF sample are added to wells 31-60, and aliquots of the sputum sample are added to wells 61-90. Wells 91-93 serve as positive controls, and wells 94-96 serve as negative controls.

The following five recombinant bacteriophage are obtained: K1-5::luxAB bacteriophage, which infects *E. coli* K1 bacteria; EBN6::luxAB bacteriophage, which infects *enterococcus* bacteria; Twort::luxAB bacteriophage, which infects *staphylococcus* bacteria; Sp6::luxAB bacteriophage, which infects *Salmonella* bacteria; and RZh::luxAB bacteriophage, which infects *streptococcus* bacteria. The phages are obtained from another source or engineered in situ, using the protocol described in Example 1.

Recombinant bacteriophage suspension equivalent to about $3\times10^8$ phages/mL is added to six individual wells of the groups of 30 wells corresponding to each of the three samples collected from the patient. Since the system involves application of the same heterologous marker across phages of different specificities, a universal detection system is developed. With minor adjustments, this system is adapted for multiplex detection, e.g., wherein a plurality of samples is processed together or at the same time. The latter system is especially useful for the identification of a cohort of bacterial pathogens that are involved in the pathogenesis of a particular disease. For instance, pathogens associated with urinary tract infections (UTI), such as *E. coli, Klebsiella, Enterobacter, Pseudomonas, Staphylococcus, Proteus*, can all be identified and characterized using the multiplex array format.

Example 4

Determination of Antimicrobial Susceptibility or Resistance of a Bacterial Sample Biological samples are diluted with 4.0 mL of LB broth and incubated at 37° C. for 4 hours to promote growth of the bacteria contained in the samples. The primary cultures are aliquoted evenly into Eppendorf tubes containing LB media supplemented with one of the following test antibiotic substances: ampicillin (penicillin class), imipenem (β-lactam antibiotic), cefoxitin (cephamycin class), ciprofloxacin (fluoroquinolone class), kanamycin (aminoglycoside class) and tetracycline (tetracycline class). After treatment with the antibiotic, the tubes are centrifuged, and the bacterial pellets are washed and re-suspended in LB broth containing phage particles containing a reporter gene. The phage-bacteria mixture is cultured under standard conditions to permit transformation of the bacteria and generation of secondary cultures. The secondary cultures are centrifuged and the bacterial pellets are lysed with a lysis buffer. The amount or activity of the reporter gene product (heterologous protein) is assayed using a standard technique, e.g., an ELISA to assess the amount of the reporter heterologous protein or an enzymatic assay to assess the activity of the reporter gene product (heterologous protein). The experiment may be performed in a singular or multiplex format.

The basic outline for the singular assay and the multiplex assay is presented in Table 4.1 below. Expected outcomes are presented in Table 4.2.

TABLE 4.1

Basic experimental set up (multiplex format is in bold)

| Detection | Sample | Step 1 = cells growth incubation | Step 2 = peptide marker expression incubation | Step 3 = peptide marker detection immunoassay |
|---|---|---|---|---|
| Single | Bacteria A, B, . . . N | +media | (None) | +anti peptide X/protein X |
| | | +media | +phage A/gene X | +anti peptide X/protein X |
| | | +media +antibiotic | +phage A/gene X | +anti peptide X/protein X |
| | | +media +antibiotic | +phage A/gene X | +anti peptide X/protein X |
| Multiplex | Bacteria A, B, . . . N | +media | (None) | +anti peptide X/protein X; anti peptide Y/protein Y |
| | | +media | +phage A/gene X; phage B/gene Y | +anti peptide X/protein X; anti peptide Y/protein Y |
| | | +media +antibiotic | +phage A/gene X; phage B/gene Y | +anti peptide X/protein X; anti peptide Y/protein Y |
| | | +media +antibiotic | +phage A/gene X; phage B/gene Y | +anti peptide X/protein X; anti peptide Y/protein Y |

TABLE 4.2

Expected results of the immunoassay (multiplex format is in bold)

| Step 3 = Immunoassay | Reaction outcome | Result |
|---|---|---|
| +anti peptide X/protein X | No signal is observed (negative control) | Control |
| +anti peptide X/protein X | peptide X/protein X (signal is observed if sample contains target A) | ID test |
| +anti peptide X/protein X | peptide X/protein X expressed by resistant strain (signal is observed if target is drug-resistant); | AST test |
| +anti peptide X/protein X | peptide X/protein X not expressed by sensitive strain (no signal if target is drug-sensitive) | negative |
| +anti peptide X/protein X; anti peptide Y/protein Y | No signal is observed (negative control) | Control |
| +anti peptide X/protein X; anti peptide Y /protein Y | Peptide X/protein X; Peptide Y/protein Y | ID test |
| +anti peptide X/protein X; anti peptide Y/protein Y | Proteins X & Y expressed by resistant strains (both signals are observed if targets are drug-resistant); | AST test |

TABLE 4.2-continued

Expected results of the immunoassay (multiplex format is in bold)

| Step 3 = Immunoassay | Reaction outcome | Result |
|---|---|---|
| +anti peptide X/protein X; anti peptide Y/protein Y | Proteins X and Y not expressed by sensitive strains (no signal or partial signal if target is drug-sensitive) | negative |

Example 5

Method for Antibacterial Susceptibility Testing

The basic experimental setup of Example 4 is retained, except that multiple batches of test samples are treated with increasing log concentrations of the same antibiotic, e.g., a final concentration of 0.00 mg/L (control), 0.01 mg/L, 0.03 mg/L, 0.10 mg/L, 0.30 mg/L, 1.0 mg/L, 3.0 mg/L, 10 mg/L, 30 mg/L, 100 mg/L ampicillin. The minimal inhibitory concentration (MIC) curve for ampicillin is ascertained for each individual species of bacteria for each of the individual test compounds tested. Species or strains that are related to one another can be compared, e.g., with regard to 50% lethal dose ($LD_{50}$) of the antibiotic and/or MIC values of the bacteria and also growth parameters, e.g., effect of the antibiotic on doubling time, etc.

Example 6

Method for Detection of *Bacillus Thuringiensis* Cry1Ab Toxin

A lateral flow immunoassay for detection of Cry1Ab protein toxin of *Bacillus thuringiensis* (Bt) as a marker protein is prepared using commercially available antibodies to detect Cry1Ab in the form of purified protein and plasmid encoded protein from lysed *E. coli* cells. The ability of the method to directly identify the pathogen and ascertain its antimicrobial susceptibility (ID/AST) from urine is assessed and compared to standard protocols provided by guidelines of Clinical and Laboratory Standards Institute (CLSI) designed for antimicrobial susceptibility testing (AST).

A lateral flow immunoassay is prepared using commercial anti-Bt Cry1Ab rabbit polyclonal antibodies and murine monoclonal antibodies (MyBioSource). Detection of Cry1Ab using the lateral flow immunoassay is compared to detection of Cry1Ab using a commercially available ELISA kit (AMAR Immunodiagnostics, catalog number AID007). The lateral flow immunoassay has generic capture and detector reagents to allow efficient screening of marker-specific antibodies. The capture reagent is composed of anti-fluorescein monoclonal antibodies immobilized on a support membrane. The detector reagent is streptavidin-coated europium nanoparticles (ThermoFisher). Marker-specific antibodies are labeled with fluorescein and biotin using commercial reagents, fluorescein isothiocyanate and biotin-NHS ester, and tested for pairing in lateral flow immunoassay format with purified Bt Cry1Ab protein. Key immunoassay parameters—concentrations of capture and detector reagents, composition of assay buffers and blockers, sample volume—are optimized with purified Bt Cry1Ab protein (UniProt P0A370) from MyBioSource.

The ability of the lateral flow immunoassay to detect Cry1Ab protein produced by *E. coli* cells harboring Cry1Ab protein expression vector (pCry1Ab-ET30a) is assessed. The test system is calibrated with purified Bt Cry1Ab protein (MyBioSource #MBS537737) and the limit of detection is computed as concentration of Cry1Ab protein corresponding to signal of [blank sample signal +3 SD] using standard curve with purified protein.

Cry1Ab protein expression in *E. coli* cells, its extracellular release from lysed cells and the CFU/mL limits of detection are assessed. The gene encoding Cry1Ab is synthesized (Epoch Life Sciences) and subcloned into pET30a (Novagen). pET30a is a protein expression vector under the transcriptional control of T7 RNA polymerase 1. pCry1Ab-ET30 is transformed into *E. coli* B and infected with T7 phage. T7 infection induces Cry1Ab expression (by supplying RNA polymerase 1), and after 30-45 minutes post-infection, lyses the cells releasing Cry1Ab. Presence of phage-induced Cry1Ab expression and release from lysed cells is determined using the lateral flow immunoassay. Detection capability is assessed using serial dilutions of cells ranging from 102 to 106 CFU/mL with a constant 108 PFU/mL. As only phage-infected lysed cells result in Cry1Ab in the supernatant, this strategy of using phage-induced plasmid-borne expression of Cry1Ab provides a useful benchmark for subsequent experiments.

Other embodiments: The preceding examples can be repeated with similar success by substituting the generically or specifically described reactants and/or operating conditions described elsewhere in the specification for those used in the preceding examples.

Example 7

Method for Detection of Urinary Tract Infection

A diagnostic assay for diagnosis of a urinary tract infection that identifies the bacteria present is described in this example. The assay was comprised of i) recombinant phage for recognition of target bacterium and for using the target bacterium to express a heterologous protein marker, and a lateral flow immunoassay for detection of the heterologous protein marker. The assay is contemplated for use with a clinical sample, e.g., urine, that is incubated with a reagent that contains an antibiotic and the recombinant phage to form a mixture; after incubation, the mixture is applied to the lateral flow immunoassay to determine presence or absence of the heterologous marker. Antibiotic-susceptible bacterial strains are inhibited by antibiotic and do not express the marker and the lateral flow immunoassay generates no signal (negative result), while antibiotic resistant bacterial strains produce marker and will result in a detectable signal (positive result) on the lateral flow immunoassay.

As a model for recombinant phage that express histidine-tagged biotinylated luciferase as a heterologous protein marker, recombinant *E. coli* cells that express constructs for His-tagged luciferase with biotin or a biotin-like moiety (streptavidin-binding protein (SBP) and TwinStrep-Tag®) were prepared. These six recombinant cell lines were designated HM50NanoSBPHis, HM50NanoHisSBP, HM50HisTwinStrept, HM50TwinStreptHis, HM50HisBiotin, HM50BiotinHis. Lysates were prepared from each cell line with Y-PER Plus protein extraction reagent.

A lateral flow immunoassay was constructed with the following regions on a nitrocellulose substrate in an upstream to downstream position: a reagent pad with the capture and detector reagents of, respectively, a murine antibody against His-tag and europium particles coated with streptavidin; a test zone composed of a negative control line of goat antibody, a test line with goat antibody against murine IgG, and a procedural control line of biotinylated bovine serum albumin (BSA); and an absorbent pad.

Diluted extracts of the cell lysates were placed on lateral flow immunoassays and signal at the lines in the test zone was read with an instrument. Detectable signal was observed from lysates of cells designated as HM50BiotinHis, HM50HisBiotin and HM50NanoHisSBP. The cells that express HM50HisBiotin provided the highest amount of detectable his-luciferase-biotin signal.

From the foregoing description, one skilled in the art can easily ascertain the essential characteristics of the methods and, without departing from the spirit and scope thereof, can make various changes and modifications to adapt it to various usages and conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to scientific databases (e.g., NCBI, GENBANK, EBI) that are hereby incorporated by reference.

It is claimed:

1. A method for simultaneously testing for the presence of a plurality of bacterial species of interest in a sample and determining susceptibility of the bacterial species of interest to an antimicrobial agent in a multiplex format, the multiplex format method comprising:
   (a) providing:
      (i) a sample,
      (ii) one or more antimicrobial agents having known antimicrobial activity specific for the bacterial species of interest;
      (iii) a plurality of recombinant bacteriophage, wherein each of the recombinant bacteriophage comprises a nucleic acid encoding a heterologous protein marker, wherein the heterologous protein marker comprises a chemiluminescent label,
      wherein each of the recombinant bacteriophage is host-specific for one of the bacterial species of interest, and wherein the heterologous protein marker is expressible upon bacteriophage transduction into said bacterial species of interest,
   (b) removing portions of the sample to generate a plurality of sample aliquots;
   (c) culturing the plurality of sample aliquots in the presence or absence of the antimicrobial agent to generate a plurality of primary culture aliquots;
   (d) exposing each of the primary culture aliquots to a different recombinant bacteriophage from the plurality of bacteriophage specific to one of the bacterial species of interest, thereby creating a plurality of secondary cultures; and
   (e) detecting the presence or absence of the chemiluminescent label directly in a cell lysate from each of the secondary cultures, wherein the presence of the chemiluminescent label in the secondary culture indicates the presence of the bacterial species of interest in the sample and resistance of that bacterial species to the antimicrobial agent; wherein detecting the chemiluminescent label comprises placing the cell lysate directly on a lateral flow immunoassay and detecting a signal on the lateral flow immunoassay from the chemiluminescent label.

2. A method for simultaneously testing for the presence of a plurality of bacterial species of interest in a sample and determining susceptibility of the bacterial species of interest to an antimicrobial agent in a multiplex format, the multiplex format method comprising:
   (a) providing:
      (i) a sample,
      (ii) one or more antimicrobial agents having known antimicrobial activity specific for the bacterial species of interest;
      (iii) a plurality of recombinant bacteriophage, wherein each of the recombinant bacteriophage comprises a nucleic acid encoding a heterologous protein marker, wherein the heterologous protein marker comprises a chemiluminescent label,
      wherein each of the recombinant bacteriophage is host-specific for one of the bacterial species of interest, and wherein the heterologous protein marker is expressible upon bacteriophage transduction into said bacterial species of interest,
   (b) generating a set of at least two primary cultures, wherein generating the primary cultures comprises:
      (i) culturing a first aliquot of said sample in the presence of the antimicrobial agent, thereby generating a first primary culture, and
      (ii) culturing a second aliquot of said sample in the absence of the antimicrobial agent, thereby generating a second primary culture;
   (c) generating a set of at least two secondary cultures, wherein generating the secondary cultures comprises:
      (i) culturing a portion of the first primary culture in the presence of one of the recombinant bacteriophage specific to one of the bacterial species of interest, thereby generating a first secondary culture, and
      (ii) culturing a portion of the second primary culture in the presence of the recombinant bacteriophage specific to one of the bacterial species of interest, thereby generating a second secondary culture; and
   (d) detecting the presence or absence of the chemiluminescent label directly in a cell lysate from the first and second secondary cultures, wherein detecting the chemiluminescent label comprises placing the cell lysate directly on a lateral flow immunoassay and detecting a signal on the lateral flow immunoassay from the chemiluminescent label;
   wherein detecting the presence of the chemiluminescent label in the second secondary culture and absence or reduced level of the heterologous protein marker in the first secondary culture indicates the presence of the bacterial species of interest in the sample, and susceptibility of the bacterial species of interest to the antimicrobial agent.

3. A method for screening to identify a test agent having antimicrobial activity for a bacterial species of interest, the method comprising:
(a) providing:
  (i) a test agent,
  (ii) a culture of a bacterial species of interest, and
  (iii) a recombinant bacteriophage comprising a nucleic acid encoding a heterologous protein marker, wherein the heterologous protein marker comprises a chemiluminescent label,
    wherein the recombinant bacteriophage is transducible for the bacterial species of interest, and wherein the heterologous protein marker is expressible upon bacteriophage transduction into said bacterial species of interest;
(b) generating primary bacterial cultures, said step comprising:
  (i) generating a first primary culture by culturing the bacterial species of interest in the presence of the test agent, and
  (ii) generating a second primary culture by culturing the bacterial species of interest in the absence of the test agent;
(c) generating secondary bacterial cultures, said step comprising:
  (i) generating a first secondary culture by exposing the first primary culture to the recombinant bacteriophage, and
  (ii) generating a second secondary culture by exposing the second primary culture to the recombinant bacteriophage;
(d) detecting a signal that correlates with expression of the chemiluminescent label directly in a cell lysate from the first and second secondary cultures, wherein detecting the chemiluminescent label comprises placing the cell lysate directly on a lateral flow immunoassay and detecting a signal on the lateral flow immunoassay from the chemiluminescent label; and,
(e) comparing the signals detected in the first and second secondary cultures, thereby identifying a test agent having antimicrobial activity for the bacterial species of interest.

4. The method of claim 3, wherein a reduction in the signal that correlates with the chemiluminescent label in the first secondary culture compared to the signal that correlates with the chemiluminescent label in the second secondary culture indicates that the test agent has antimicrobial activity for the bacterial species of interest.

5. The method of claim 3, wherein a uniformity or an increase in the signal that correlates with the chemiluminescent label in the first secondary culture compared to the level or activity of the chemiluminescent label in the second secondary culture (control) indicates that the test agent does not have antimicrobial activity for the bacterial species of interest.

6. The method of claim 3, wherein the bacterial species of interest are selected from the group consisting of gram positive or gram negative bacteria.

7. The method of claim 6, wherein the bacterial species of interest is selected from the group consisting of *Acinetobacter baumannii*, *Bacillus anthracis*, *Bacillus cereus*, *Bordetella pertussis*, *Borrelia burgdorferi*, *Brucella aborus*, *Brucella canis*, *Brucella melitensis*, *Brucella suis*, *Campylobacter jejuni*, *Chlamydia pneumoniae*, *Chlamydia psittaci*, *Chlamydia trachomatis*, *Clostridium botulinum*, *Clostridium difficile*, *Clostridium perfringens*, *Clostridium tetani*, *Corynebacterium diphtheriae*, *Enterobacter* sp., *Enterococcus faecalis*, vancomycin-resistant *Enterococcus faecalis*, *Enterococcus faecium*, *Escherichia coli*, enterotoxigenic *Escherichia coli* (ETEC), enteropathogenic *Escherichia coli*, *E. coli* O157:H7, *Francisella tularensis*, *Haemophilus influenzae*, *Helicobacter pylori*, *Klebsiella pneumoniae*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitidis*, *Proteus*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermis*, *Staphylococcus saprophyticus*, methicillin-resistant *Staphylococcus aureus* (MRSA), vancomycin-resistant *Staphylococcus aureus* (VSA), *Streptococcus agalactiae*, *Streptococcus pneumoniae*, *Streptococcus pyogenes*, *Treponema pallidum*, *Vibrio cholerae*, and *Yersinia pestis* or a combination thereof.

8. The method of claim 3, wherein the bacterial species of interest are selected from the group consisting of *Bacillus anthracis*, *Bacillus subtilis*, *Bacillus thuringiensis*, *Escherichia coli*, *Lactobacillus delbrueckii*, *Lactobacillus plantarum*, *Lactococcus lactis*, *Listeria monocytogenes*, *Pseudomonas aeruginosa*, *Pseudomonas syringae*, *Klebsiella*, *Salmonella*, *Shigella*, and *Staphylococcus aureus*.

9. The method of claim 3, further comprising validating the detecting of a signal that correlates with expression of the chemiluminescent label by detecting a secondary marker which is a nucleic acid marker selected from the group consisting of DNA, RNA or a combination thereof.

10. The method of claim 9, wherein the level of the secondary marker is detected with gel-electrophoresis, polymerase chain reaction (PCR), quantitative polymerase chain reaction (qPCR) or a combination thereof.

11. The method of claim 3, wherein the bacterial species of interest is a pathogenic bacterial species associated with urinary tract infections (UTI).

12. The method of claim 3, wherein the bacterial species of interest is selected from *E. coli* sp., *Klebsiella* sp., *Enterobacter* sp., *Pseudomonas* sp., *Staphylococcus* sp. and *Proteus* sp.

13. The method of claim 3, wherein detecting a signal comprises quantitating a signal.

14. The method of claim 1, wherein the chemiluminescent label comprises a histidine-tagged luciferase.

15. The method of claim 14, wherein the lateral flow immunoassay comprises an antibody that binds the histidine-tagged luciferase.

16. The method of claim 2, wherein the chemiluminescent label comprises a histidine-tagged luciferase.

17. The method of claim 16, wherein the lateral flow immunoassay comprises an antibody that binds the histidine-tagged luciferase.

18. The method of claim 3, wherein the chemiluminescent label comprises a histidine-tagged luciferase.

19. The method of claim 18, wherein the lateral flow immunoassay comprises an antibody that binds the histidine-tagged luciferase.

20. The method of claim 19, wherein the antibody that binds the histidine-tagged luciferase is a murine antibody specific for the histidine tag.

* * * * *